(12) United States Patent
Laggner et al.

(10) Patent No.: US 8,470,867 B2
(45) Date of Patent: Jun. 25, 2013

(54) SIGMA RECEPTOR INHIBITORS

(75) Inventors: Christian Laggner, Maria Enzersdorf (AT); María Rosa Cuberes-Altisent, Cugat de Vallés (ES); Joerg Holenz, Vilanova i la Geltrú (ES); Juana María Berrocal-Romero, Cornella de Llobregat (ES); Maria Montserrat Contijoch-Llobet, Terrasa (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 176 days.

(21) Appl. No.: 12/703,112

(22) Filed: Feb. 9, 2010

(65) Prior Publication Data

US 2010/0190780 A1 Jul. 29, 2010

Related U.S. Application Data

(63) Continuation of application No. 11/574,361, filed as application No. PCT/EP2005/009375 on Aug. 29, 2005, now Pat. No. 7,696,199, which is a continuation-in-part of application No. 10/978,250, filed on Oct. 29, 2004, now abandoned.

(30) Foreign Application Priority Data

Aug. 27, 2004 (EP) .................................... 04077421
Oct. 14, 2004 (ES) .................................... 200402441

(51) Int. Cl.
*C07D 231/22* (2006.01)

(52) U.S. Cl.
USPC ................... 514/407; 548/366.4; 548/370.1; 548/371.1

(58) Field of Classification Search
USPC ........................................ 548/366.1, 370.1
See application file for complete search history.

(56) References Cited

U.S. PATENT DOCUMENTS

| 4,337,263 | A | 6/1982 | Techer et al. |
| 5,948,777 | A | 9/1999 | Bender et al. |
| 6,100,259 | A | 8/2000 | Xiang et al. |
| 6,492,529 | B1 | 12/2002 | Kapadia et al. |
| 2003/0144309 | A1 | 7/2003 | Choon-Moon |
| 2006/0106068 | A1 | 5/2006 | Laggner |

FOREIGN PATENT DOCUMENTS

| EP | 0414289 A1 | 2/1991 |
| EP | 0431943 A2 | 6/1991 |
| EP | 0445974 A2 | 9/1991 |
| EP | 0518805 | 12/1992 |
| FR | 2301250 | 9/1976 |
| FR | 2472564 | 7/1981 |
| GB | 1088973 | 10/1967 |
| JP | 10055048 A | 2/1998 |
| WO | WO 91/09594 | 7/1991 |
| WO | WO 00/27394 A | 5/2000 |
| WO | WO 0027394 A1 * | 5/2000 |
| WO | WO 02/092573 | 11/2002 |
| WO | WO 02/102387 | 12/2002 |
| WO | WO 2004/016592 A1 | 2/2004 |
| WO | WO 2004/017961 A2 | 3/2004 |
| WO | WO 2004046129 A2 * | 6/2004 |
| WO | WO 2005/061462 A2 | 7/2005 |

OTHER PUBLICATIONS

Arthritis [online], [retrieved on Nov. 20, 2007]. Retrieved from the Internet, URL; http://www.nlm.nih.gov/medlineplus/ency/article/001243.htm>.
Cancer [online], [retrieved on Jul. 6, 2007]. Retrieved from the Internet, URL; http://www.nim.nih.gov/medlineplus/cancer.html>.
Cancer [online], [retrieved on Jul. 6, 2007]. Retrieved from the Internet, URL; http://en.wikipedia.org/wiki/Cancer>.
*Cancer and Metastasis Reviews*, 17(1), 91-106, 1998.
DeHaven-Hudkins, D. et al., "Characterization of the binding of [$^3$H](+)-pentazocine to σ recognition sites in guinea pig brain," *Eur. J. Pharmacol.*, vol. 227: 371-378, 1992.
Epilepsy [online], [retrieved on Nov. 20, 2007]. Retrieved from the Internet, URL; http://www.nim.nih.gov/medlineplus/ency/article/000694.htm>.
European Patent Office, European Search Report for EP 04077421.8, dated Feb. 1, 2005.
Hanner, M. et al., "Purification, molecular cloning, and expression of the mammalian sigma$_1$-binding site," *Proc. Natl. Acad. Sci.*, vol. 93: 8072-8077, Jul. 1996.
Isomers [on-line], [retrieved on Mar. 11, 2007]. Retrieved from the Internet, URL; http://chemed.chem.purdue.edu/genchem/topicreview/bp/1organic/isomers.html>.
Langa, F. et al., "Generation and phenotypic analysis of sigma receptor type I (σ1) knockout mice," *European Journal of Neuroscience*, vol. 18: 2188-2196, 2003.

(Continued)

*Primary Examiner* — Yong Chu
(74) *Attorney, Agent, or Firm* — Locke Lord LLP

(57) ABSTRACT

The invention relates to compounds of formula (I) having pharmacological activity towards the sigma receptor, to processes of preparation of such compounds, to pharmaceutical compositions comprising them, and to their use for the treatment and or prophylaxis of a disease in which the sigma receptor is involved.

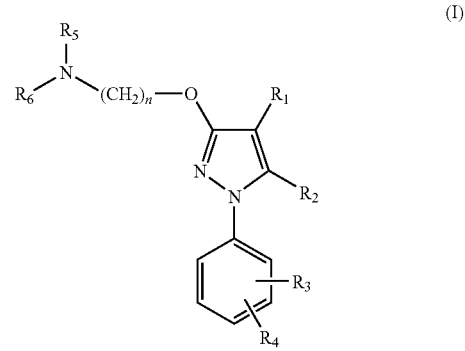

14 Claims, 3 Drawing Sheets

OTHER PUBLICATIONS

Lowry, O.H. et al., "Protein Measurement With the Folin Phenol Reagent," *J. Biol. Chem.*, pp. 265-275, 1951.
Prodrug [online], [retrieved on Mar. 11, 2007. Retrieved from the Internet, URL; http://en.wikipedia.org/wiki/Prodrug>.
Quirion, R. et al., "A proposal for the classification of sigma binding sites," *Trends Pharmacol. Sci.*, vol. 13: 85-86, 1992.
Radesca, L. et al., "Synthesis and Receptor Binding of Enantiomeric N-Substituted cis-N-[2-(3,4-Dichlorophenyl)ethyl]-2-(1-pyrrolidinyl) cyclohexylamines as High-Affinity σ Receptor Ligands," *J. Med. Chem.*, vol. 34: 3058-3065, 1991.
Rossiter et al., "Copper (II)-Mediated Arylation with Aryl Boronic Acids for the N-Derivatization of Pyrazole Libraries," J. Comb. Chem., 2004, vol. 6, pp. 385-390, published on web Feb. 5, 2004.
Schoeffter, P. et al., "Functional, Endogenously expressed 5-hydroxytryptamine 5-ht$_7$ Receptors in Human Vascular Smooth Muscle Cells," *British Journal of Pharmacology*, vol. 117: 993-994, 1996.
*Science*, 286: 531-537, 1999.
Snyder, S.H. et al., "Receptor Mechanisms in Antipsychotic Drug Action: Focus on Sigma Receptors," *Journal of Neuropsychiatry*, vol. 1: 7-15, 1989.
Vippagunta et al., *Advanced Drug Delivery Reviews*, 48: 1-26, 2001.
Walker, J.M., et al., "Sigma Receptors: Biology and Function," *Pharmacological Reviews*, vol. 42: 355-402, 1990.
Wu et al., Regulatory Perspectives of Type II Prodrug Development and Time-Dependent Toxicity Management: Nonclinical Pharm/Tox Analysis and the Role of Comparative Toxicology, *Toxicology*, 236: 1-6, 2007.
International Search Report as issued on Jan. 12, 2005 in related international application PCT/EP2005/009375.
International Preliminary Report on Patentability as issued on Feb. 28, 2007 in related international application PCT/EP2005/009375.
Written Opinion of the International Searching Authority as issued on Nov. 29, 2005 in related international application PCT/EP2005/009375.
Requirement for Restriction/Election as issued on Apr. 5, 2007 in related priority U.S. Appl. No. 10/978,250.
Non-Final Office Action as issued on Jun. 14, 2007 in related priority U.S. Appl. No. 10/978,250.
Final Office Action as issued on Nov. 29, 2007 in related priority U.S. Appl. No. 10/978,250.
Non-Final Office Action as issued on Apr. 16, 2008 in related priority U.S. Appl. No. 10/978,250.
Final Office Action as issued on Oct. 20, 2008 in related priority U.S. Appl. No. 10/978,250.
U.S. Appl. No. 12/703,126, filed Feb. 9, 2010, Christian Laggner.
U.S. Appl. No. 12/703,114, filed Feb. 9, 2010, Christian Laggner.
U.S. Appl. No. 12/620,273, filed Nov. 17, 2009, Christian Laggner.

* cited by examiner

SIGMA RECEPTOR INHIBITORS

This application is a continuation of U.S. application Ser. No. 11/574,361, filed Aug. 9, 2007 and issued as U.S. Pat. No. 7,696,199, which is a national stage entry under 35 U.S.C. §371 of International Application No. PCT/EP2005/009375 filed on Aug. 29, 2005, which is a continuation-in-part of U.S. application Ser. No. 10/978,250, filed on Oct. 29, 2004 and subsequently abandoned; and also which claims benefit of Spanish Patent Application No. P200402441, filed on Oct. 14, 2004 and European Patent Application No. 04077421.8, filed on Aug. 27, 2004, which are all incorporated by reference in their entireties.

FIELD OF THE INVENTION

The present invention relates to compounds having pharmacological activity towards the sigma (σ) receptor, and more particularly to some pyrazole derivatives, to processes of preparation of such compounds, to pharmaceutical compositions comprising them, and to their use in therapy and prophylaxis, in particular for the treatment of psychosis.

BACKGROUND OF THE INVENTION

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews,* 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.,* 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Set.,* 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

European patent application EP 0 414 289 A1 generically discloses a class of 1,2,3,4-tetrahydro-spiro[naphthalene-1, 4'-piperidine] and 1,4-dihydro-spiro[naphthalene-1,4'-piperidine] derivatives substituted at the piperidine N-atom with a hydrocarbon group alleged to have selective sigma receptor antagonistic activity. The term hydrocarbon, as defined in said patent, covers all possible straight chained, cyclic, heterocyclic, etc. groups. However, only compounds having benzyl, phenethyl, cycloalkylmethyl, furyl- or thienylmethyl or lower alkyl or alkenyl as the hydrocarbon substituent at the piperidine nitrogen atom are specifically disclosed. The compounds are stated to displace tritiated di-tolyl guanidine (DTG) from sigma sites with potencies better than 200 nM. 1'-benzyl-1,2,3,4-tetrahydro-spiro[naphthalene-1,4'-piperidine] is mentioned as a particularly preferred compound.

European patent application EP 0 445 974 A2 generically describes the corresponding spiro[indane-1,4'-piperidine] and spiro[benzocycloheptene-5,4'-piperidine] derivatives. Again the compounds are only stated to displace tritiated di-tolyl guanidine (DTG) from sigma sites with potencies better than 200 nM.

European patent Application EP0 431 943 A relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the spiro cyclic ring system. Of the remainder compounds, the main part has another polar substituent attached to the Spiro nucleus and/or they have some polar substituents in the substituent on the piperidine N-atom. No suggestion or indication of effect of the compounds on the sigma receptor is given.

Patent applications EP 518 805 A and WO 02/102387 describe sigma receptor ligands having piperidine or spiropiperidine structures.

With regard to the chemical structure of the compounds described in the present patent application, there are some documents in the prior art which disclose pyrazole derivatives characterized, among other things, for being substituted by amino alkoxy groups in different positions of the pyrazole group.

U.S. Pat. No. 4,337,263 discloses 1-aryl-4-aryl sulphonyl-3-amino propoxy-1H-pyrazoles, wherein the amino group can be constituted by an N-cycle group as morpholine, piperidine or pyrrolidine group. They are used as hypolipemiant or hypocholesteroleminant agents.

Patent FR 2301250 describes similar compounds as those mentioned above, such as 1,4-diaryl-3-aminoalcoxy pyrazoles, wherein the amino group comprises pyrrolidine, piperidine, hydroxypiperidine, morpholine or piperazine derivatives.

Patent Application US2003/0144309 refers to pyrazoles with their 3 position substituted by a dimethylaminoethoxy group and present in their 4 position a pirimidine group. They are used as inhibitors of JNK3, Lck or Src kinase activity.

International patent Application WO 02/092573 describes substituted pirazole compounds as inhibitors of SRC and other protein kinases.

International patent Application WO 2004/017961 discloses pyrazol compounds wherein the 3 position is substituted by an alcoxy group directly bounded to a cyclic amide, which are used for therapeutically treating and/or preventing a sex hormone related condition in a patient.

U.S. Pat. No. 6,492,529 describes pyrazole derivatives which are used for the treatment of inflammatory diseases. These compounds present in the 5 position a urea group, linked in some cases to a morpholine ethoxy group.

International patent Application WO 04/016592 refers to pyrazole compounds for inhibiting protein prenylation which comprises in the 5 position, among others, an alcoxy group directly bonded to a cyclic amide.

However, none of these documents suggests the effect of these compounds on the sigma receptor.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of structurally distinct pyrazol derivatives which are particularly selective inhibitors of the sigma receptor. The compounds present a pyrazol group which are characterized by the substitution at position 3 by an alkoxy group directly bounded to a nitrogen.

In one aspect the invention is directed to a compound of the formula I:

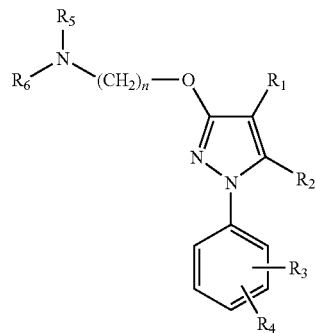

(I)

wherein
 $R_1$ is selected from the group formed by hydrogen, substituted or unsubstituted alkyl, substituted or unsubstituted cycloalkyl, substituted or unsubstituted alkenyl, substituted or unsubstituted arylalkyl, substituted or unsubstituted non-aromatic heterocyclyl, substituted or unsubstituted heterocyclylalkyl, —$COR_8$, —$C(O)OR_8$, —$C(O)NR_8R_9$ —$C=NR_8$, —$CN$, —$OR_8$, —$OC(O)R_8$, —$S(O)_tR_8$, —$NR_8R_9$, —$NR_8C(O)R_9$, —$NO_2$, —$N=CR_8R_9$, or halogen;
 $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, or halogen;
 $R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, or halogen, or together they form a fused ring system,
 $R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C=NR_8$, —$CN$, —$OR_8$, —$OC(O)R_8$, —$S(O)_t$—$R_8$—$NR_8R_9$, —$NR_8C(O)R_9$, —$NO_2$, —$N=CR_8R_9$, or halogen; together form, with the nitrogen atom to which they are attached, a substituted or unsubstituted heterocyclyl group;
 n is selected from 1, 2, 3, 4, 5, 6, 7 or 8;
 t is 1, 2 or 3;
 $R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;
or a pharmaceutically acceptable salt, isomer, prodrug or solvate thereof.

In a second aspect the invention is directed to a compound of the formula IB:

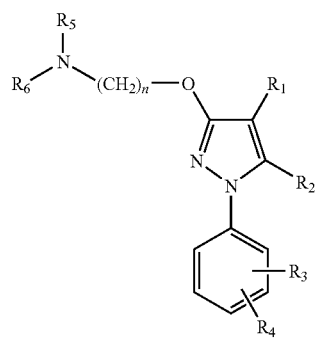

(IB)

wherein
 $R_1$ is selected from the group formed by substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted non-aromatic heterocyclyl, substituted or unsubstituted heterocyclylalkyl, —$COR_8$, —$C(O)OR_8$, —$C(O)NR_8R_9$ —$C=NR_8$, —$CN$, —$OR_8$, —$OC(O)R_8$, —$NR_8R_9$, —$NR_8C(O)R_9$, —$NO2$, —$N=CR_8R_9$ or halogen,
 $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C=NR_8$, —CN, —$OR_8$, —$OC(O)R_8$, —$S(O)_t$—$R_8$—$NR_8R_9$, $NR_8C(O)R_9$, —$NO_2$, —$N=CR_8R_9$, or halogen;

$R_3$ and $R_4$ are independently selected from the group formed by substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C=NR_8$, —CN, —$OR_8$, —$OC(O)R_8$, —$S(O)_tR_8$, —$NR_8R_9$, —$NR_8C(O)R_9$, —NO2, —$N=CR_8R_9$, or halogen, or together they form a fused ring system, $R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C=NR_8$, —CN, —$OR_8$, —$OC(O)R_8$, —$S(O)_tR_8$—$NR_8R_9$, —$NR_8C(O)R_9$, —$NO_2$, —$N=CR_8R_9$, or halogen; together form, with the nitrogen atom to which they are attached, a substituted or unsubstituted heterocyclyl group;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

or a pharmaceutically acceptable salt, isomer, prodrug or solvate thereof.

In one embodiment $R_1$ in formula I above is selected from H, —$COR_8$, or substituted or unsubstituted alkyl, preferably it is selected from H, methyl or acetyl.

In a preferred embodiment in the compound of formula (I), $R_1$ is hydrogen.

In another embodiment $R_2$ is preferably alkyl, most preferably methyl.

In another embodiment $R_2$ is preferably H.

In another embodiment $R_1$ and $R_2$ do not form together a fused ring system.

In one embodiment $R_3$ and $R_4$ are halogen or alkyl. In a more preferred embodiment they are halogen or haloalkyl.

It is preferred that the aryl substituents $R_3$ and $R_4$ are situated in the meta and/or para positions of the phenyl group.

Further, in a preferred embodiment n is preferably 2, 3, 4, 5, or 6 most preferably n is 2, 3 or 4. A most preferred value for n is 2.

In another preferred embodiment $R_5$ and $R_6$, together, form a morpholine-4-yl group.

In another aspect the invention is directed to a process for the preparation of a compound of formula (I) or (IB) or a salt, isomer or solvate thereof.

In another aspect the invention is directed to a pharmaceutical composition which comprises a compound as above defined or a pharmaceutically acceptable salt, enantiomer, prodrug or solvate thereof, and a pharmaceutically acceptable carrier, adjuvant or vehicle. In a further aspect the invention is directed to the use of a compound of formula I or IB for the treatment or prophylaxis of a sigma receptor mediated disease or condition.

In another preferred embodiment the compounds as above defined are used in the manufacture of a medicament for the treatment of diarrhoea, lipoprotein disorders, migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety or schizophrenia; inflammation, autoimmune diseases; or to the use as pharmacological tool, as anxiolytic or as immunosuppressant.

In a more preferred embodiment the medicament is for the treatment of pain, more preferably neuropathic pain or allodynia.

The above mentioned preferences and embodiments can be combined to give further preferred compounds or uses.

BRIEF DESCRIPTION OF THE FIGURES

FIG. 2 proofs the dose dependency of the treatment with the compound of example 1 (VII) to show analgesia in capsaicin-induced neuropathic pain.

FIG. 3 demonstrates that the treatment with the compound of example 1 (VII) is effective specifically in neuropathic pain or mechanical allodynia as shown by the efficacy depending on the force of the von-Frey filaments with 0.5 g being typically in the range of neuropathic pain/allodynia.

DETAILED DESCRIPTION OF THE INVENTION

Figure 1:
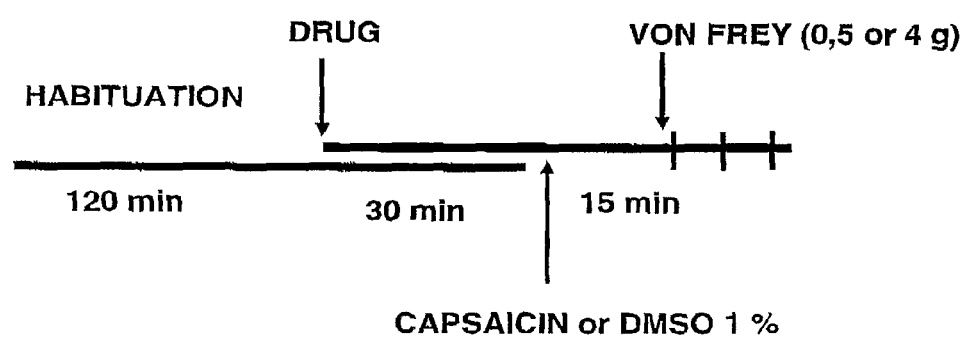
FIG. 1 refers to the test protocol for all tests with von Frey filaments.

The typical compounds of this invention effectively and selectively inhibit the sigma receptor.

In the present description the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2 C atoms and having one or more unsaturated bonds.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarin, morpholine; pyrrole, pyrazole, oxazole, isoxazole, triazole, imidazole, etc.

"Alkoxy" refers to a radical of the formula —ORa where Ra is an alkyl radical as defined above, e.g., methoxy, ethoxy, propoxy, etc.

"Amino" refers to a radical of the formula —NH2, —NHRa or —NRaRb, optionally quaternized.

"Halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Particular individual compounds of the invention falling under formula (I) include the compounds listed below:

Ex1 4-{2-(1-(3,4-Dichlorophenyl)-5-methyl-1H pyrazol-3-yloxy)ethyl}morpholine (VII), Ex2 2-[1-(3,4-Dichlorophenyl)-5-methyl-1H-pyrazol-3-yloxy]-N,N-diethylethanamine hydrochloride Ex3 1-(3,4-Dichlorophenyl)-5-methyl-3-[2-(pyrrolidin-1-yl)ethoxy]-1H-pyrazole hydrochloride Ex4 1-(3,4-Dichlorophenyl)-5-methyl-3-[3-(pyrrolidin-1-yl)propoxy]-1H-pyrazole hydrochloride Ex5 1-{2-[1-(3,4-Dichlorophenyl)-5-methyl-1H-pyrazol-3-yloxy]ethyl}piperidine Ex6 1-{2-[1-(3,4-dichlorophenyl)-5-methyl-1H-pyrazol-3-yloxy]ethyl}-1H-imidazole Ex7 3-{1-[2-(1-(3,4-Dichlorophenyl)-5-methyl-1H-pyrazol-3-yloxy)ethyl]piperidin-4-yl}-3H-imidazo[4,5-b]pyridine Ex8 1-{2-[1-(3,4-Dichlorophenyl)-5-methyl-1H-pyrazol-3-yloxy]ethyl}-4-methylpiperazine Ex9 Ethyl 4-{2-[1-(3,4-dichlorophenyl)-5-methyl-1H-pyrazol-3-yloxy]ethyl}piperazine carboxylate Ex10 1-(4-(2-(1-(3,4-dichlorophenyl)-5-methyl-1H-pyrazol-3-yloxy)ethyl)piperazin-1-yl)ethanone Ex11 4-{2-[1-(4-Methoxyphenyl)-5-methyl-1H-pyrazol-3-yloxy]ethyl}morpholine hydrochloride Ex12 1-(4-Methoxyphenyl)-5-methyl-3-[2-(pyrrolidin-1-yl)ethoxy]-1H-pyrazole Ex13 1-(4-Methoxyphenyl)-5-methyl-3-[3-(pyrrolidin-1-yl)propoxy]-1H-pyrazole Ex14 1-[2-(1-(4-Methoxyphenyl)-5-methyl-1H-pyrazol-3-yloxy)ethyl]piperidine Ex15 1-{2-[1-(4-Methoxyphenyl)-5-methyl-1H-pyrazol-3-yloxy]ethyl}-1H-imidazole Ex16 4-{2-[1-(3,4-Dichlorophenyl)-5-phenyl-1H-pyrazol-3-yloxy]ethyl}morpholine hydrochloride Ex17 1-(3,4-Dichlorophenyl)-5-phenyl-3-[2-(pyrrolidin-1-yl)ethoxy]-1H-pyrazole hydrochloride Ex18 1-(3,4-Dichlorophenyl)-5-phenyl-3-[3-(pyrrolidin-1-yl)propoxy]-1H-pyrazole Ex19 1-{2-[1-(3,4-Dichlorophenyl)-5-phenyl-1H-pyrazol-3-yloxy]ethyl}piperidine Ex20 1-{2-[1-(3,4-Dichlorophenyl)-5-phenyl-1H-pyrazol-3-yloxy]ethyl}-1H-imidazole hydrochloride Ex21 2-{2-[1-(3,4-dichlorophenyl)-5-phenyl-1H-pyrazol-3-yloxy]ethyl}-1,2,3,4-tetrahydroisoquinoline hydrochloride Ex22 4-{4-[1-(3,4-Dichlorophenyl)-5-methyl-1H-pyrazol-3-yloxy]butyl}morpholine hydrochloride Ex23 1-(3,4-Dichlorophenyl)-5-methyl-3-[4-(pyrrolidin-1-yl)butoxy]-1H-pyrazole Ex24 1-{4-[1-(3,4-Dichlorophenyl)-5-methyl-1H-pyrazol-3-yloxy]butyl}piperidine hydrochloride Ex25 1-{4-[1-(3,4-Dichlorophenyl)-5-methyl-1H-pyrazol-3-yloxy]butyl}-4-methylpiperazine dihydrochloride Ex26 1-{4-[1-(3,4-Dichlorophenyl)-5-methyl-1H-pyrazol-3-yloxy]butyl}-1H-imidazole Ex27 4-[1-(3,4-Dichlorophenyl)-5-methyl-1H-pyrazol-3-yloxy]-N,N-diethylbutan-1-amine Ex28 1-{4-[1-(3,4-dichlorophenyl)-5-methyl-1H-pyrazol-3-yloxy]butyl}-4-phenylpiperidine hydrochloride Ex29 1-{4-[1-(3,4-dichlorophenyl)-5-methyl-1H-pyrazol-3-yloxy]butyl}-6,7-dihydro-1H-indol-4(5H)-one Ex30 2-{4-[1-(3,4-dichlorophenyl)-5-methyl-1H-pyrazol-3-yloxy]butyl}-1,2,3,4-tetrahydroisoqui-noline Ex31 4-{2-[1-(3,4-dichlorophenyl)-5-isopropyl-1H-pyrazol-3-yloxy]ethyl}morpholine hydrochloride
Ex32 2-[1-(3,4-Dichlorophenyl)-5-isopropyl-1H-pyrazol-3-yloxy]-N,N-diethylethanamine
Ex33 1-(3,4-Dichlorophenyl)-5-isopropyl-3-[2-(pyrrolidin-1-yl)ethoxy]-1H-pyrazole hydrochloride
Ex34 1-(3,4-Dichlorophenyl)-5-isopropyl-3-[3-(pyrrolidin-1-yl)propoxy]-1H-pyrazole hydrochloride
Ex35 1-{2-[1-(3,4-Dichlorophenyl)-5-isopropyl-1H-pyrazol-3-yloxy]ethyl}piperidine
Ex36 2-{2-[1-(3,4-dichlorophenyl)-5-isopropyl-1H-pyrazol-3-yloxy]ethyl}-1,2,3,4-tetrahydroisoqui-noline hydrochloride
Ex37 4-{2-[1-(3,4-dichlorophenyl)-1H-pyrazol-3-yloxy]ethyl}morpholine
Ex37.HCl 4-{2-[1-(3,4-dichlorophenyl)-1H-pyrazol-3-yloxy]ethyl}morpholine hydrochloride
Ex38 2-[1-(3,4-dichlorophenyl)-1H-pyrazol-3-yloxy]N,N-diethylethanamine
Ex38HCl 2-[1-(3,4-dichlorophenyl)-1H-pyrazol-3-yloxy]N,N-diethylethanamine hydrochloride
Ex39 1-(3,4-dichlorophenyl)-3-[2-(pyrrolidin-1-yl)ethoxy]-1H-pyrazole
Ex39HCl 1-(3,4-dichlorophenyl)-3-[2-(pyrrolidin-1-yl)ethoxy]-1H-pyrazole hydrochloride
Ex40 1-{2-[1-(3,4-dichlorophenyl)-1H-pyrazol-3-yloxy]ethyl}piperidine
Ex40HCl 1-{2-[1-(3,4-dichlorophenyl)-1H-pyrazol-3-yloxy]ethyl}piperidine hydrochloride
Ex41 1-(3,4-dichlorophenyl)-3-[3-(pyrrolidin-1-yl)propoxy]-1H-pyrazole
Ex41HCl 1-(3,4-dichlorophenyl)-3-[3-(pyrrolidin-1-yl)propoxy]-1H-pyrazole hydrochloride
Ex 42 1-{2-[1-(3,4-Dichlorophenyl)-5-methyl-1H-pyrazol-3-yloxy]ethyl}piperazine dihydrochloride
Ex 43 1-{2-[1-(3,4-Dichlorophenyl)-5-methyl-1H-pyrazol-3-yloxy]ethyl}pyrrolidin-3-amine
Ex 44 4-{2-[1-(3,4-Dichlorophenyl)-4,5-dimethyl-1H-pyrazol-3-yloxy]ethyl}morpholine
Ex 44HCl 4-{2-[1-(3,4-Dichlorophenyl)-4,5-dimethyl-1H-pyrazol-3-yloxy]ethyl}morpholine hydrochloride
Ex 45 2-[1-(3,4-Dichlorophenyl)-4,5-dimethyl-1H-pyrazol-3-yloxy]-N,N-diethylethanamine hydrochloride
Ex 46 1-(3,4-Dichlorophenyl)-4,5-dimethyl-3-[2-(pyrrolidin-1-yl)ethoxy]-1H-pyrazole hydrochloride
Ex 47 1-(3,4-Dichlorophenyl)-4,5-dimethyl-3-[3-(pyrrolidin-1-yl)propoxy]-1H-pyrazole hydrochloride
Ex 48 1-{2-[1-(3,4-Dichlorophenyl)-4,5-dimethyl-1H-pyrazol-3-yloxy]ethyl}piperidine
Ex 49 4-{4-[1-(3,4-dichlorophenyl)-1H-pyrazol-3-yloxy]butyl}morpholine hydrochloride
Ex 50 (2S,6R)-4-{4-[1-(3,4-dichlorophenyl)-1H-pyrazol-3-yloxy]butyl}-2,6-dimethylmorpholine hydrochloride
Ex 51 1-{4-[1-(3,4-Dichlorophenyl)-1H-pyrazol-3-yloxy]butyl}piperidine hydrochloride
Ex 52 1-(3,4-Dichlorophenyl)-3-[4-(pyrrolidin-1-yl)butoxy]-1H-pyrazole hydrochloride
Ex 53 4-[1-(3,4-dichlorophenyl)-1H-pyrazol-3-yloxy]-N,N-diethylbutan-1-amine oxalate
Ex 54 N-benzyl-4-[1-(3,4-dichlorophenyl)-1H-pyrazol-3-yloxy]-N-methylbutan-1-amine oxalate
Ex 55 4-[1-(3,4-dichlorophenyl)-1H-pyrazol-3-yloxy]-N-(2-methoxyethyl)-N-methylbutan-1-amine oxalate
Ex 56 4-{4-[1-(3,4-dichlorophenyl)-1H-pyrazol-3-yloxy]butyl}thiomorpholine oxalate
Ex 57 1-[1-(3,4-Dichlorophenyl)-5-methyl-3-(2-morpholinoethoxy)-1H-pyrazol-4-yl]ethanone oxalate
Ex 58 1-{1-(3,4-dichlorophenyl)-5-methyl-3-[2-(pyrrolidin-1-yl)ethoxy]-1H-pyrazol-4-yl}ethanone oxalate
Ex 59 1-{1-(3,4-dichlorophenyl)-5-methyl-3-[2-(piperidin-1-yl)ethoxy]-1H-pyrazol-4-yl}ethanone oxalate
Ex 60 1-{1-(3,4-dichlorophenyl)-3-[2-(diethylamino)ethoxy]-5-methyl-1H-pyrazol-4-yl}ethanone oxalate
Ex 61 4-{2-[5-Methyl-1-(naphthalen-2-yl)-1H-pyrazol-3-yloxy]ethyl}morpholine
Ex 62 N,N-Diethyl-2-[5-methyl-1-(naphthalen-2-yl)-1H-pyrazol-3-yloxy]ethanamine
Ex 63 1-{2-[5-Methyl-1-(naphthalen-2-yl)-1H-pyrazol-3-yloxy]ethyl}piperidine hydrochloride
Ex 64 5-Methyl-1-(naphthalen-2-yl)-3-[2-(pyrrolidin-1-yl)ethoxy]-1H-pyrazole hydrochloride their salts, different alternative pharmaceutically acceptable salts, solvates or prodrugs.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bio availability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) or (IB) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

The compounds of the invention may be in crystalline form either as free compounds or as solvates and it is intended that both faiths are within the scope of the present invention. Methods of solvation are generally known within the art. Suitable solvates are pharmaceutically acceptable solvates. In a particular embodiment the solvate is a hydrate.

The compounds of formula (I), or (IB) or their salts or solvates are preferably in pharmaceutically acceptable or substantially pure fowl. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or (IB), or of its salts, solvates or prodrugs.

The compounds of the present invention represented by the above described formula (I) or (IB) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds of formula (I) or (IB) defined above can be obtained by available synthetic procedures similar to those described in the U.S. Pat. No. 4,337,263 or FR 2 472 564. For example, they can be prepared by condensing a compound of Formula (II):

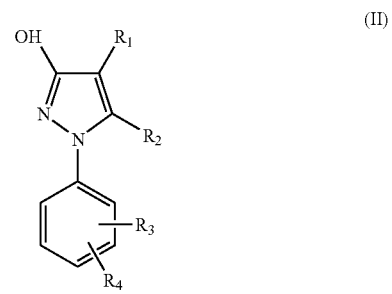

in which $R_1$-$R_4$ are as defined above in formulae (I), with a compound of Formula (III):

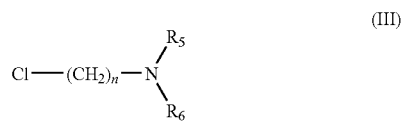

in which $R_5$, $R_6$ and n are as defined above in formula (I).

The reaction of compounds of formulas (II) and (III) is preferably carried out at a temperature in the range of 60 to 120° C. in an aprotic solvent, but not limited to, such as dimethylformamide (DMF) in the presence of an inorganic base, such as $K_2CO_3$.

A general scheme for synthesizing compounds (II), (I) or (IB) is:

General Scheme of Synthesis

Scheme I

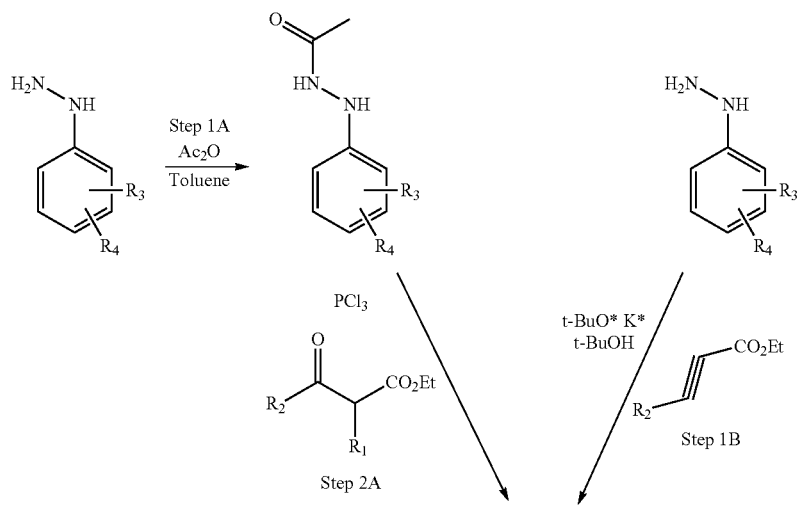

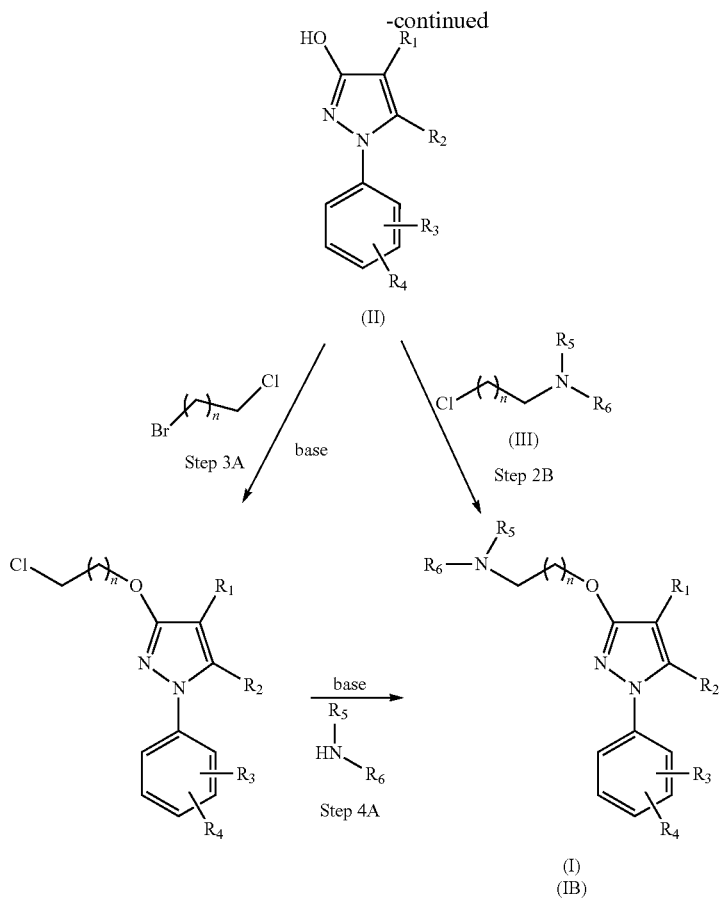

The intermediate compound (II) can also be prepared as described in the bibliography (see L. F. Tietze et al., Synthesis, (11), 1079-1080, 1993; F. Effenberger and W. Hartmann, Chem. Ber., 102(10), 3260-3267, 1969; both cites incorporated here by reference). It can also be prepared by conventional methods, as can be seen in the synthetic examples of the present patent application.
Compounds of Formula (III) are commercially available or can be prepared by conventional methods.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such fowl in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing a sigma receptor mediated disease which method comprises administering to a patient in need of such a treatment a therapeutically effective amount of a compound as above defined or a pharmaceutical composition thereof. Among the sigma mediated diseases that can be treated are diarrhoea, lipoprotein disorders, migraine, obesity, arthritis, hypertension, arrhythmia, ulcer, cognition disorders, addiction to chemical substances such as cocaine dependency, tardive diskinesia, ischemic stroke, epilepsy, stroke, depression, stress, pain, especially neuropathic pain or allodynia, psychotic condition or cancer. The compounds of the invention can also be employed as pharmacological tool or as anxiolytic or immunosuppressant.

The term "pharmacological tool" refers to the property of compounds of the invention through which they are particularly selective ligands for Sigma receptors which implies that compound of formula I, described in this invention, can be used as a model for testing other compounds as Sigma ligands, ex. a radiactive ligands being replaced, and can also be used for modeling physiological actions related to Sigma receptors.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

Example 1

Synthesis of 4-{2-(1-(3,4-Dichlorophenyl)-5-methyl-1H pyrazol-3-yloxy)ethyl}morpholine (VII)

Step 1: Synthesis of Acetic Acid N'-(3,4-Dichlorophenyl)hydrazide (V)

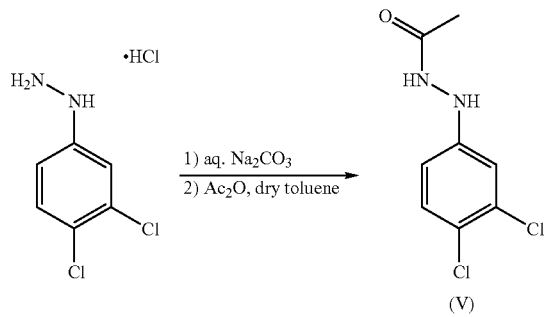

N'-(3,4-Dichlorophenyl)hydrazine was liberated from its hydrochloride (10.0 g, 46.8 mmol) by partitioning the solid between diluted $Na_2CO_3$ solution (10 ml saturated solution and 40 ml water) and AcOEt. The aqueous layer was extracted two more times with AcOEt, the organic extracts were dried ($Na_2SO_4$), the solvent was removed in vacuo, and the residue was taken up in dry toluene (100 ml). To this solution acetic anhydride (4.78 g, 46.8 mmol) was slowly added, and the reaction mixture was stirred at room temperature for 15 min. Light petroleum (50 ml) was added, the mixture was cooled in the refrigerator (−20° C.), and the resulting crystals were collected on a sintered glass funnel and washed with cold petrol ether. Recrystallization from MeOH yielded (V) (8.30 g, 81%) as shiny white crystals, mp 179-182° C. (lit. 168-171° C.). TLC $CHCl_3$/MeOH 9:1.

MS m/z (%): 222/220/218 (W, 3/22/34), 178 (64), 176 (100), 160 (20), 43 (94).

Only the NMR signals of the dominant isomer are given (ratio ca. 9:1):

$^1$H-NMR (DMSO-$d_6$): (ppm) 9.69 (d, 11-1, NH—CO, $^3J$=2.0 Hz), 8.09 (d, 1H, Ph-NH, $^3J$=2.0 Hz), 7.32 (d, 1H, Ph 1-1-5, $^3J$(H5, 1-16)=8.8 Hz), 6.83 (d, 1H, Ph H-2, $^4J$(H2,H6)= 2.5 Hz), 6.66 (dd, 1H, Ph H-6, $^4$3(H2,146) 2.5 Hz, $^3J$(H5, H6)=8.8 Hz), 1.90 (s, 31-1, Me).

$^{13}$C-NMR (DMSO-$d_6$): S (ppm) 169.2 (C=O), 149.6 (Ph C-1), 131.2 (Ph C-3), 130.5 (Ph C-5), 119.1 (Ph C-4), 112.9 (Ph C-2*), 112.4 (Ph C-6*), 20.6 (Me).

Step 2: Synthesis of 1-(3,4-Dichlorophenyl)-5-methyl-4H-pyrazol-3-ol (VI)

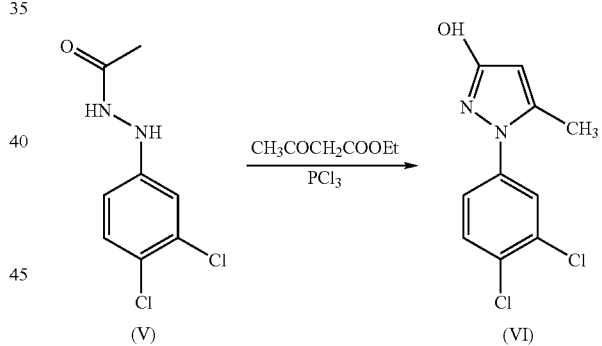

To a mixture of (V) (5.0 g, 22.8 mmol) and ethyl acetoacetate (2.97 g 22.8 mmol) was slowly added $PCl_3$ (3.13 g, 22.8 mmol). The mixture was warmed to 50° C. for 1.5 h, poured into ice water (150 ml), and the resulting precipitate was collected on a sintered glass funnel and recrystallized from EtOH to yield (VI) (2.29 g, 41%) as white crystals, mp 208-211° C. (lit. 208-209° C.), TLC $CHCl_3$/MeOH 9:1.

MS m/z (%): 246/244/242 (M+, 11/59/100), 207 (32), 147 (20), 145 (34), 111 (20), 109 (23), 75 (20).

$^1$H-NMR (CDCl3): S (ppm) 11.72 (broad s, 1H, OH), 7.54 (d, 1H, Ph H-5, 3J(H5,H6)=8.5 Hz), 7.48 (d, 1H, Ph 11-2, 4J(H2,H6) −2.5 Hz), 7.26 (dd, 1H, Ph H-6, 4J(H2,H6)=2.5 Hz, 3J(H5,H6)=83 Hz), 5.63 (s, 1H, 4-H), 2.28 (s, 3H, 5-Me).

$^{13}$C-NMR (CDCl$_3$): 6 (ppm) 163.1 (Pz C-3), 141.2 (Pz C-5), 137.9 (Ph C-1), 133.1 (Ph C-3), 131.4 (Ph C-4), 131.0 (Ph C-5), 126.1 (Ph C-2), 123.6 (Ph C-6), 94.5 (Pz C-4), 12.7 (5-Me).

Step 3: Synthesis of 4-{2-(1-(3,4-Dichlorophenyl)-5-methyl-1H pyrazol-3-yloxy)ethyl}morpholine (VII)

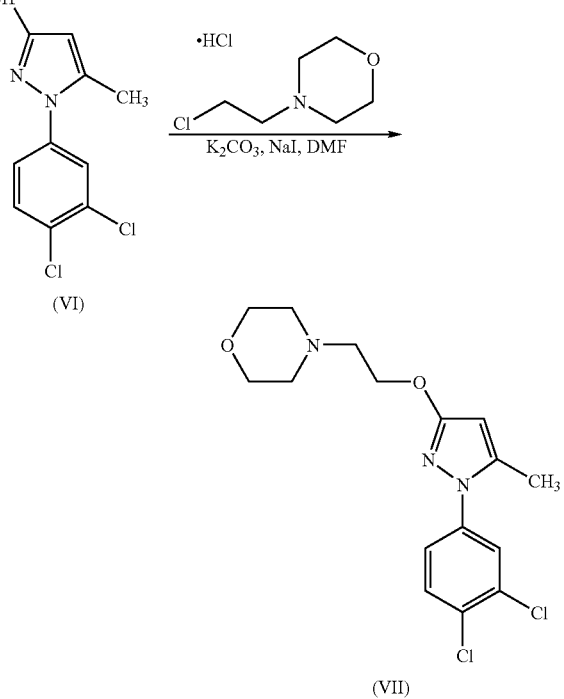

A mixture of (VI) (300 mg, 1.23 mmol), N-(2-chloroethyl) morpholine hydrochloride (230 mg, 123 mmol), K$_2$CO$_3$ (341 mg, 2.47 mmol), and NaI (185 mg, 1.23 mmol) in dry dimethyl formamide (5 ml) was stirred overnight at 70° C. The mixture was poured into water (20 ml), extracted four times with Et$_2$O, and the organic extracts were washed with saturated NaCl solution, dried (Na$_2$SO$_4$), and concentrated in vacuo. The residue was purified via MPLC (light petroleum/AcOEt 4:1) to yield (VII) (303 mg, 69%) as a colorless oil. TLC CHCl$_3$/MeOH 9:1.

MS m/z (%): 357/355 (Mt, 0.03/0.05), 114 (19), 113 (100), 100 (92), 98 (16), 56 (21).

$^1$H-NMR (CDCl3): S (ppm) 7.57 (d, 1H, Ph H-2, 4J(H2, H6)=2.5 Hz), 7.47 (d, 1H, Ph H-5, 3J(H5,H6) 8.6 Hz), 726 (dd, 1H, Ph H-6, 4.1 (H2,H6)=2.5 Hz, 3J(H5,H6)=8.6 Hz), 5.68 (s, 1H, 4-H), 4.31 (t, 2H, O—CHz, 3J=5.6 Hz), 3.72 (m, 4H, Morph H-2,6), 2.77 (t, 2H, CH-Morph, 3J-5.6 Hz), 2.55 (m, 411, Morph H-3,5), 2.30 (s, 3H, 5-Me).

$^{13}$C-NMR (CDC13): S (ppm) 163.4 (Pz C-3), 140.5 (Pz C-5), 139.1 (Ph C-1), 132.9 (Ph C-3), 130.5 (Ph C-5), 130.3 (Ph C-4), 125.7 (Ph C-2), 122.7 (Ph C-6), 94.5 (Pz C-4), 66.8 (Morph C-2,6), 65.9 (O—CH2), 57.6 (CH2-Morph), 53.9 (Morph C-3,5), 13.1 (5-Me).

Anal. Calcd for C16H19C12N302: C, 53.94; H, 5.38; N, 11.79. Found: C, 53.85; H, 5.13; N, 11.57.

Example 2

2-[1-(3,4-Dichlorophenyl)-5-methyl-1H-pyrazol-3-yloxy]-N,N-diethylethanamine hydrochloride

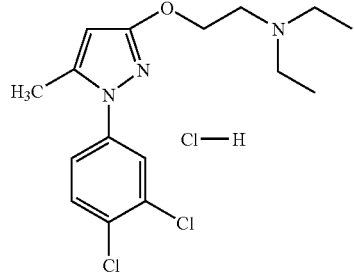

Beige colour amorphous solid. Yield=64%
$^1$H-NMR (DMSO-d$_6$) δ ppm: 10.0 (br s, 1H), 7.8 (d, J=1.7 Hz, 1H), 7.7 (d, J=8.7 Hz, 1H), 7.5 (dd, J=1.7 and 7.8 Hz, 1H), 5.9 (s, 1H), 4.5 (t, J=4.8 Hz, 2H), 3.45 (m, 2H), 3.2 (m, 4H), 2.3 (s, 3H), 1.2 (t, 6H)

Example 3

1-(3,4-Dichlorophenyl)-5-methyl-3-[2-(pyrrolidin-1-yl)ethoxy]-1H-pyrazole hydrochloride

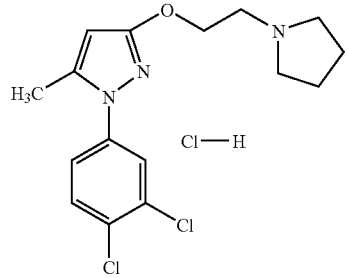

White-yellow solid. M.p.>280° C. (decomp.). Yield 37.5%
$^1$H-NMR (DMSO-d$_6$) δ ppm: 10.4 (br s, 1H), 7.8 (d, J=2.5 Hz, 1H), 7.7 (d, 3-8.8 Hz, 1H), 7.5 (dd, J=2.5 and 8.8 Hz, 1H), 5.9 (s, 1H), 4.45 (t, J=4.7 Hz, 2H), 3.5 (m, 4H), 3.05 (m, 2H), 2.4 (s, 3H), 1.8-1.95 (m, 4H).

Example 4

1-(3,4-Dichlorophenyl)-5-methyl-3-[3-(pyrrolidin-1-yl)propoxy]-1H-pyrazole hydrochloride

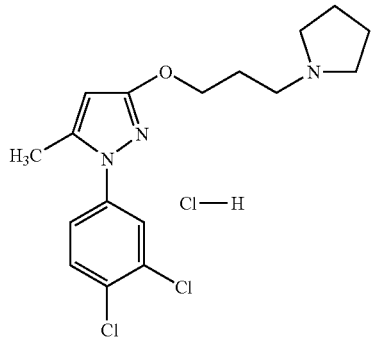

White solid. M.p.=149-155° C. Yield=51%
$^1$H-NMR (DMSO-d$_6$) δ ppm: 10.05 (br s, 1H), 7.75 (d, J=2.6 Hz, 1H), 7.7 (d, J=7.8 Hz, 1H), 7.5 (d, J=7.8 Hz, 1H), 5.8 (s, 1H), 4.2 (m, 2H), 3.5 (m, 2H), 3.3 (m, 2H), 3.0 (m, 2H), 2.3 (s, 3H), 1.8-2.1 (m, 6H).

Example 5

1-{2-[1-(3,4-dichlorophenyl)-5-methyl-1H-pyrazol-3-yloxy]ethyl}piperidine

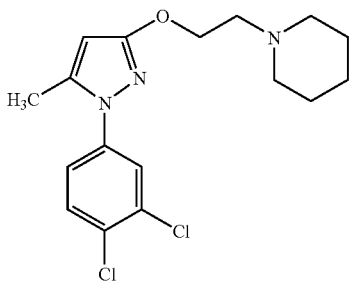 [SMILES: Cc1cc(OCCN2CCCCC2)nn1-c1ccc(Cl)c(Cl)c1]

White solid. M.p.=119-122° C. Yield=46%
$^1$H-NMR (CDCl$_3$) δ ppm: 7.55 (d, J=2.4 Hz, 1H), 7.5 (d, J=8.8 Hz, 1H), 7.3 (dd, J=2.4 and 8.8 Hz, 1H), 5.7 (s, 1H), 4.6 (m, 2H), 2.7-3.2 (m, 4H), 2.3 (s, 3H), 1.4-1.9 (m, 8H).

Example 6

1-{2-[1-(3,4-dichlorophenyl)-5-methyl-1H-pyrazol-3-yloxy]ethyl}-1H-imidazole

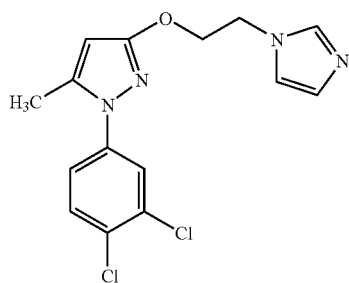 [SMILES: Cc1cc(OCCn2ccnc2)nn1-c1ccc(Cl)c(Cl)c1]

White solid. M.p.=111-112° C. Yield=54%
¹H-NMR (DMSO-d₆) δ ppm: 7.75 (d, J=2.3 Hz, 1H), 7.7 (d, J=8.7 Hz, 1H), 7.6 (s, 1H), 7.5 (dd, J=2.3 and 8.7 Hz, 1H), 7.2 (s, 1H), 6.9 (s, 1H), 5.8 (s, 1H), 4.3 (m, 4H), 2.3 (s, 3H)

Example 7

3-{1-[2-(1-(3,4-Dichlorophenyl)-5-methyl-1H-pyrazol-3-yloxy)ethyl]piperidin-4-yl}-3H-imidazo[4,5-b]pyridine

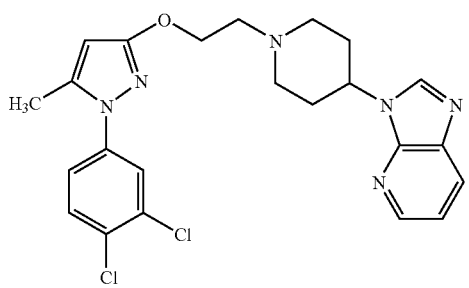 [SMILES: Cc1cc(OCCN2CCC(n3cnc4cccnc43)CC2)nn1-c1ccc(Cl)c(Cl)c1]

White solid. M.p.=104-107° C. Yield=44%
¹H-NMR (CDCl₃) δ ppm: 8.4 (dd, J=1.3 and 4.8 Hz, 1H), 8.2 (s, 1H), 8.1 (dd, J=1.3 and 8.1 Hz, 1H), 7.55 (d, J=2.5 Hz, 1H), 7.5 (d, J=8.7 Hz, 1H), 7.3-7.2 (m+solvent, 2H), 5.7 (s, 1H), 4.75-4.5 (m, 3H), 3.5-3.0 (m, 4H), 2.9-2.4 (m, 2H), 2.3 (m+s, 5H), 1.6 (m, 2H).

Example 8

1-{2-[1-(3,4-Dichlorophenyl)-5-methyl-1H-pyrazol-3-yloxy]ethyl}-4-methylpiperazine

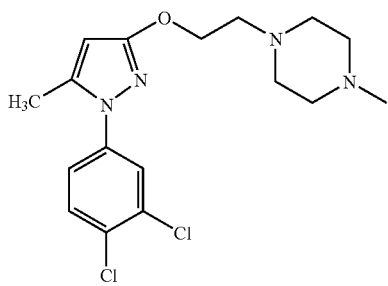

Oil. Yield=35%
¹H-NMR (CDCl₃) δ ppm: 7.55 (d, J=2.5 Hz, 1H), 7.5 (d, J=8.7 Hz, 1H), 7.3 (dd, J=2.5 and 8.7 Hz, 1H), 5.7 (s, 1H), 4.3 (t, J=5.6 Hz, 2H), 2.8 (t, J=5.6 Hz, 2H), 2.7 (m, 8H), 2.4 (s, 3H), 2.3 (s, 3H).

Example 9

Ethyl 4-{2-[1-(3,4-dichlorophenyl)-5-methyl-1H-pyrazol-3-yloxy]ethyl}piperazine carboxylate

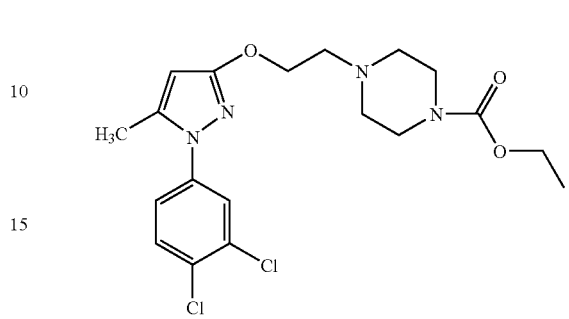

Oil. Yield=25%
¹H-NMR (CDCl₃) δ ppm: 7.55 (d, J=2.5 Hz, 1H), 7.5 (d, J=8.6 Hz, 1H), 7.3-7.2 (dd+solvent, J=2.5 and 8.6 Hz, 1H), 5.7 (s, 1H), 4.4 (bm, 2H), 4.15 (q, J=7.1 Hz, 2H), 3.6 (bm, 4H), 2.9-2.6 (bm, 6H), 2.3 (s, 3H), 1.25 (t, J=7.1 Hz, 3H).

Example 10

1-(4-(2-(1-(3,4-dichlorophenyl)-5-methyl-1H-pyrazol-3-yloxy)ethyl)piperazin-1-yl)ethanone

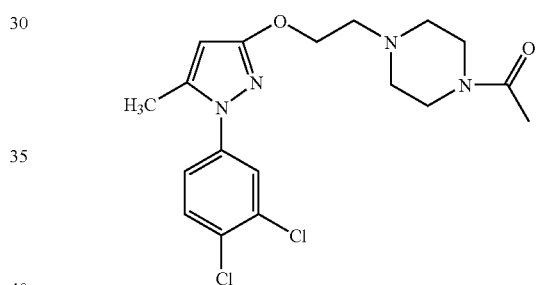

Oil. Yield=17%
¹H-NMR (CDCl₃) δ ppm: 7.55 (d, J=2.3 Hz, 1H), 7.5 (d, J=8.6 Hz, 1H), 7.3-7.2 (dd+solvent, J=2.3 and 8.6 Hz, 1H), 5.7 (s, 1H), 4.4 (bm, 2H), 3.6 (bm, 4H), 2.9-2.6 (bm, 6H), 2.3 (s, 3H), 2.1 (s, 3H).

Example 11

4-{2-[1-(4-Methoxyphenyl)-5-methyl-1H-pyrazol-3-yloxy]ethyl}morpholine hydrochloride

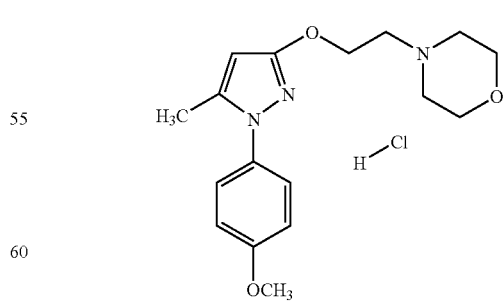

White solid. M.p. 169-173° C.
¹H-NMR (DMSO-d₆) δ ppm: 10.9 (br s, 1H), 7.35 (d, J=8.7 Hz, 2H), 7.0 (d, J=8.7 Hz, 2H), 5.8 (s, 1H), 4.5 (m, 2H), 3.7-3.9 (m, 4H), 3.8 (s, 3H), 3.4-3.55 (m, 4H), 3.1-3.2 (m, 2H), 2.2 (s, 3H).

Example 12

1-(4-Methoxyphenyl)-5-methyl-3-[2-(pyrrolidin-1-yl)ethoxy]-1H-pyrazole

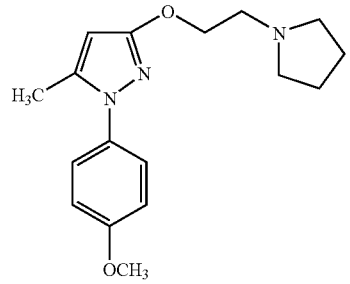 [SMILES: COc1ccc(-n2nc(OCCN3CCCC3)cc2C)cc1]

Oil. Yield=11%
$^1$H-NMR (CDCl$_3$) δ ppm: 7.3 (d, J=8.9 Hz, 2H), 6.9 (d, J=8.9 Hz, 2H), 5.65 (s, 1H), 4.3 (m, 2H), 3.8 (s, 3H), 2.9 (m, 2H), 2.65 (m, 4H), 2.2 (s, 3H), 1.8 (m, 4H).

Example 13

1-(4-Methoxyphenyl)-5-methyl-3-[3-(pyrrolidin-1-yl)propoxy]-1H-pyrazole

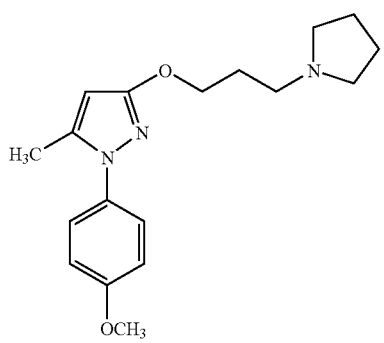 [SMILES: COc1ccc(-n2nc(OCCCN3CCCC3)cc2C)cc1]

Oil. Yield=27%
$^1$H-NMR (CDCl$_3$) δ ppm: 7.25 (d, J=8.8 Hz, 2H), 6.9 (d, J=8.8 Hz, 2H), 5.55 (s, 1H), 4.15 (t, J=6.4 Hz, 2H), 3.75 (s, 3H), 2.55 (m, 6H), 2.15 (s, 3H), 1.95 (m, 2H), 1.7 (m, 4H).

Example 14

1-[2-(1-(4-Methoxyphenyl)-5-methyl-1H-pyrazol-3-yloxy)ethyl]piperidine

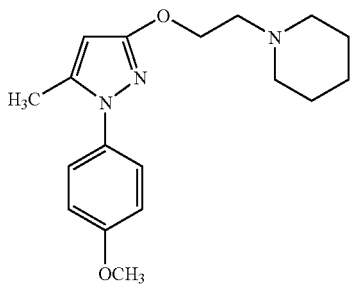 [SMILES: COc1ccc(-n2nc(OCCN3CCCCC3)cc2C)cc1]

Oil. Yield=21%
$^1$H-NMR (CDCl$_3$) δ ppm: 7.25 (d, J=8.9 Hz, 2H), 6.85 (d, J=8.9 Hz, 2H), 5.55 (s, 1H), 4.25 (m, 2H), 3.75 (s, 3H), 2.7 (m, 2H), 2.45 (m, 4H), 2.15 (s, 3H), 1.55 (m, 4H), 1.4 (m, 2H).

Example 15

1-{2-[1-(4-Methoxyphenyl)-5-methyl-1H-pyrazol-3-yloxy]ethyl}-1H-imidazole

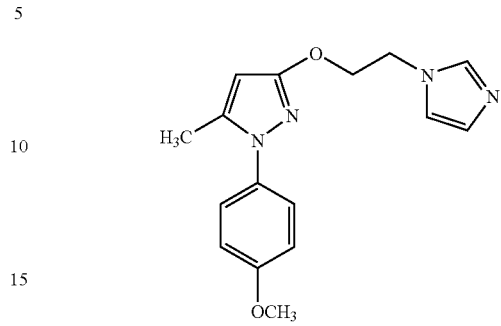

Oil. Yield=31%
$^1$H-NMR (CDCl$_3$) δ ppm: 7.6 (s, 1H), 7.25 (d, J=8.7 Hz, 2H), 7.1 (s, 1H), 7.0 (s, 1H), 6.9 (d, J=8.7 Hz, 2H), 5.6 (s, 1H), 4.45 (t, J=5.0 Hz, 2H), 4.3 (t, J=5.0 Hz, 2H), 3.8 (s, 3H), 2.2 (s, 3H).

Example 16

4-{2-[1-(3,4-Dichlorophenyl)-5-phenyl-1H-pyrazol-3-yloxy]ethyl}morpholine hydrochloride

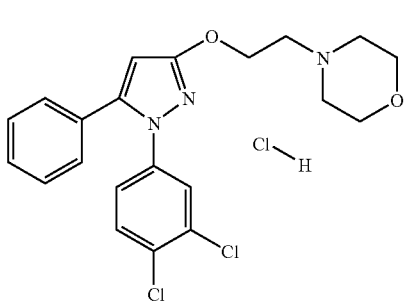 [SMILES: Clc1ccc(-n2nc(OCCN3CCOCC3)cc2-c2ccccc2)cc1Cl ; Cl]

White solid. M.p.=197-207° C. Yield=52%
$^1$H-NMR (DMSO-d$_6$) δ ppm: 10.75 (br s, 1H), 7.6 (d, J=8.6 Hz, 1H), 7.5 (d, J=2.5 Hz, 1H), 7.4 (m, 3H), 7.3 (m, 2H), 7.1 (dd, J=2.5 and 8.6 Hz, 1H), 6.3 (s, 1H), 4.6 (m, 2H), 3.95 (m, 2H), 3.75 (m, 2H), 3.4-3.55 (m, 4H), 3.2 (m, 2H).

Example 17

1-(3,4-Dichlorophenyl)-5-phenyl-3-[2-(pyrrolidin-1-yl)ethoxy]-1H-pyrazole hydrochloride

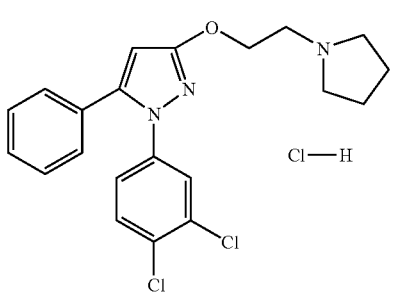

Yellow colour solid. M.p.=137-147° C. Yield=52%
$^1$H-NMR (DMSO-d$_6$) δ ppm: 10.35 (br s, 1H), 7.6 (d, J=8.7 Hz, 1H), 7.5 (d, J=2.5 Hz, 1H), 7.4 (m, 3H), 7.3 (m, 2H), 7.1 (dd, J=2.5 and 8.7 Hz, 1H), 6.3 (s, 1H), 4.5 (m, 2H), 3.6 (m, 4H), 3.1 (m, 2H), 1.85-2.0 (m, 4H).

Example 18

1-(3,4-Dichlorophenyl)-5-phenyl-3-[3-(pyrrolidin-1-yl)propoxy]-1H-pyrazole

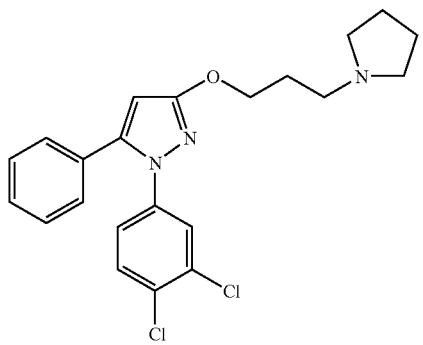 [SMILES: Clc1ccc(-n2nc(OCCCN3CCCC3)cc2-c2ccccc2)cc1Cl]

Oil. Yield=63%
$^1$H-NMR (CDCl$_3$) δ ppm: 7.5 (d, J=2.4 Hz, 1H), 7.3 (m, 3H), 7.25 (m, 3H), 6.95 (dd, J=2.4 and 8.6 Hz, 1H), 5.95 (s, 1H), 4.3 (t, J=6.4 Hz, 2H), 2.45-2.75 (m, 6H), 2.05 (m, 2H), 1.8 (m, 4H).

Example 19

1-{2-[1-(3,4-Dichlorophenyl)-5-phenyl-1H-pyrazol-3-yloxy]ethyl}piperidine

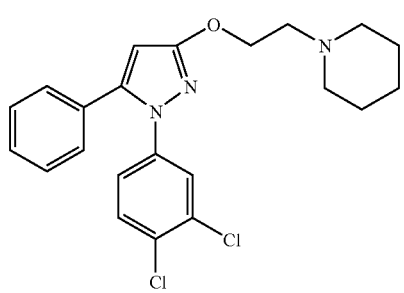 [SMILES: Clc1ccc(-n2nc(OCCN3CCCCC3)cc2-c2ccccc2)cc1Cl]

Oil. Yield=44%
$^1$H-NMR (CDCl$_3$) δ ppm: 7.45 (d, J=2.5 Hz, 1H), 7.35 (m, 3H), 7.2 (m, 3H), 6.95 (dd, J=2.5 and 8.6 Hz, 1H), 6.0 (s, 1H), 4.4 (m, 2H), 2.8 (m, 2H), 2.5 (m, 4H), 1.4-1.7 (m, 6H).

Example 20

1-{2-[1-(3,4-Dichlorophenyl)-5-phenyl-1H-pyrazol-3-yloxy]ethyl}-1H-imidazole hydrochloride

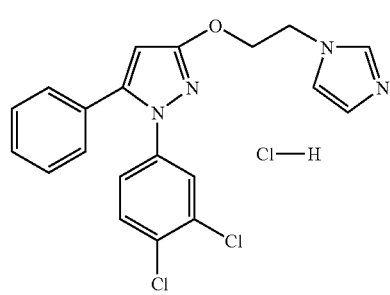

Beige colour solid. M.p.=147-155° C. Yield=44%
$^1$H-NMR (DMSO-d$_6$) δ ppm: 9.2 (s, 1H), 7.8 (s, 1H), 7.7 (s, 1H), 7.6 (d, J=8.6 Hz, 1H), 7.5 (d, J=2.4 Hz, 1H), 7.4 (m, 3H), 7.25 (m, 2H), 7.05 (dd, J=2.4 and 8.6 Hz, 1H), 6.2 (s, 1H), 4.6 (m, 4H)

Example 21

2-{2-[1-(3,4-Dichlorophenyl)-5-phenyl-1H-pyrazol-3-yloxy]ethyl}-1,2,3,4-tetrahydroisoquinoline hydrochloride

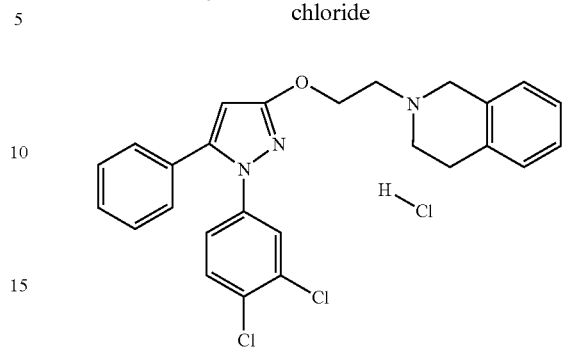

White solid. M.p.=185-189° C. Yield=34%
$^1$H-NMR (CDCl$_3$) δ ppm: 13.5 (bs, 1H), 7.4-7.2 (m, 10H), 7.1 (d, J=6.7 Hz, 1H), 6.95 (dd, J=2.5 and 8.6 Hz, 1H), 6.0 (s, 1H), 4.9 (s, 2H), 4.7 (d, J=14 Hz, 1H), 4.25 (dd, J=5.4 and 5.8 Hz, 1H), 3.8 (m, 1H), 3.6-3.4 (m, 4H), 3.1 (m, 1H).

Example 22

4-{4-[1-(3,4-Dichlorophenyl)-5-methyl-1H-pyrazol-3-yloxy]butyl}morpholine hydrochloride

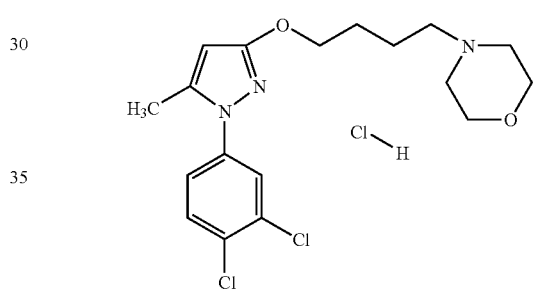

Beige colour solid. M.p.=150-154° C. Yield=28%
$^1$H-NMR (DMSO-d$_6$) δ ppm: 10.4 (br s, 1H), 7.75 (d, J=2.5 Hz, 1H), 7.7 (d, J=8.8 Hz, 1H), 7.5 (dd, J=2.5 ans 8.8 Hz, 1H), 5.8 (s, 1H), 4.1 (t, J=5.9 Hz, 2H), 3.6-3.9 (m, 4H), 3.4 (m, 2H), 3.0-3.15 (m, 4H), 2.3 (s, 3H), 1.8-1.7 (m, 4H).

Example 23

1-(3,4-Dichlorophenyl)-5-methyl-3-[4-(pyrrolidin-1-yl)butoxy]-1H-pyrazole

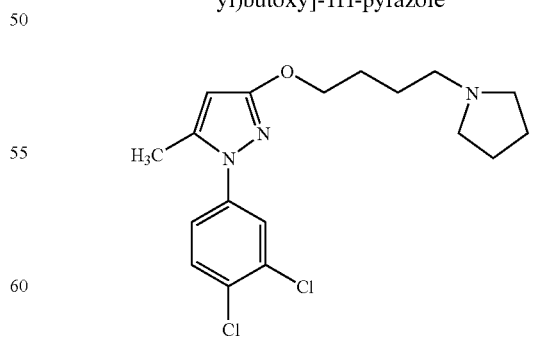

Oil. Yield=46%
$^1$H-NMR (CDCl$_3$) δ ppm: 7.55 (d, J=2.5 Hz, 1H), 7.5 (d, J=8.6 Hz, 1H), 7.3 (dd, J=2.5 and 8.6 Hz, 1H), 5.65 (s, 1H), 4.15 (t, J=6.3 Hz, 2H), 2.6 (m, 6H), 2.3 (s, 3H), 1.8 (m, 8H).

Example 24

Synthesis of 1-{4-[1-(3,4-Dichlorophenyl)-5-methyl-1H-pyrazol-3-yloxy]butyl}piperidine hydrochloride Synthesis of 3-(4-chlorobutoxy)-1-(3,4-dichlorophenyl)-5-methyl-1H-pyrazole (Scheme I, step 3A.)

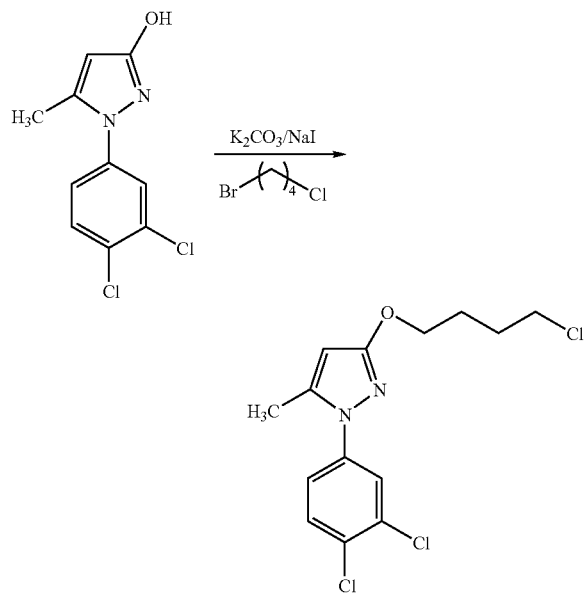

A mixture of 1-(3,4-dichlorophenyl)-5-methyl-1H-pyrazol-3-ol, obtained in step 2 of Example 1 (1.67 g, 6.87 mmol), 1-bromo-4-chlorobutane (1.58 ml, 13.74 mmol), K$_2$CO$_3$ (2.85 g, 20.6 mmol) and NaI (1.03 g, 6.87 mmol) in dry dimethylformamide (100 ml) was stirred overnight at room temperature. Solvent was evaporated in vacuo and the crude residue was partitioned between water/dichloromethane. The organic extracts were washed with saturated NaCl solution, dried on Na$_2$SO$_4$ and concentrated in vacuo to obtain 2.07 g (90%) of an oily compound, corresponding to 3-(4-chlorobutoxy)-1-(3,4-dichlorophenyl)-5-methyl-1H-pyrazole, which solidifies on standing.

$^1$H-NMR (CDCl$_3$) δ ppm: 7.6 (d, J=2.5 Hz, 1H), 7.5 (d, J=8.6 Hz, 1H), 7.3 (dd, J=2.5 and 8.6 Hz, 1H), 5.65 (s, 1H), 4.2 (t, J=5.8 Hz, 2H), 3.6 (t, 3=6.2 Hz, 2H), 2.3 (s, 3H), 1.95 (m, 4H).

Synthesis of 1-{4-[1-(3,4-dichlorophenyl)-5-methyl-1H-pyrazol-3-yloxy]butyl}piperidine hydrochloride (Scheme I, step 4A)

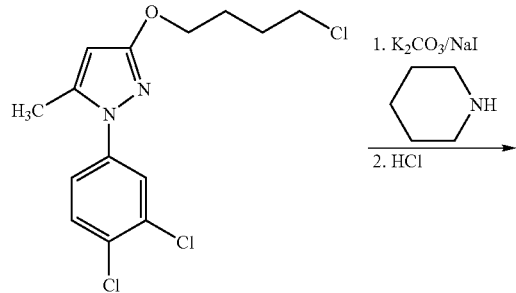

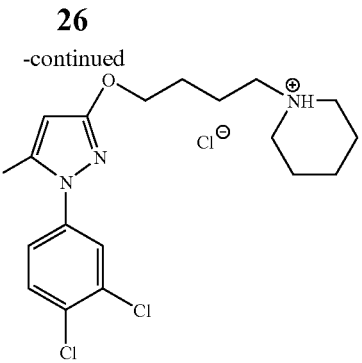

A mixture of 3-(4-chlorobutoxy)-1-(3,4-dichlorophenyl)-5-methyl-1H-pyrazole (0.1 g, 0.3 mmol), piperidine (29.5 pa, 0.3 mmol), K$_2$CO$_3$ (124 mg, 0.9 mmol) and NaI (45 mg, 0.3 mmol) in dry dimethylformamide (5 ml) and toluene (5 ml) was refluxed overnight. Solvents were evaporated in vacuo and the crude residue partitioned in water/ethylic ether. The organic extracts were washed with saturated NaCl solution, dried on Na$_2$SO$_4$ and concentrated in vacuo to obtain a crude oil, which was purified by column chromatography on silica gel (ethyl acetate/methanol 9:1).

1-{4-[1-(3,4-Dichlorophenyl)-5-methyl-1H-pyrazol-3-yloxy]butyl}piperidine, obtained as an oil, was dissolved in ethanol saturated with HCl gas and crystallized. A white solid corresponding to its hydrochloride salt was obtained.

Thus 1-{4-[1-(3,4-Dichlorophenyl)-5-methyl-1H-pyrazol-3-yloxy]butyl}piperidine hydrochloride

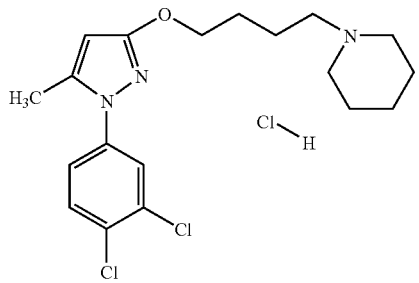

White solid. M.p.=156-161° C. Yield=32%
$^1$H-NMR (CH$_3$OH-d$_4$) δ ppm: 7.7 (d, J=2.5 Hz, 1H), 7.65 (d, 3-8.7 Hz, 1H), 7.4 (dd, J=2.5 and 8.7 Hz, 1H), 5.8 (s, 1H), 4.2 (t, J=5.7 Hz, 2H), 3.5 (m, 2H), 3.2 (m, 2H), 2.9 (m, 2H), 2.35 (s, 3H), 1.95-1.5 (m, 10H).

Example 25

1-{4-[1-(3,4-Dichlorophenyl)-5-methyl-1H-pyrazol-3-yloxy]butyl}-4-methylpiperazine dihydrochloride

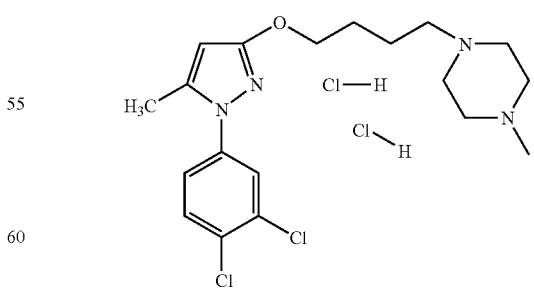

White solid. M.p.=181-185° C. Yield=32%
$^1$H-NMR (DMSO-d$_6$) δ ppm: 11.7 (br s, 2H), 7.8 (d, J=2.5 Hz, 1H), 7.7 (d, J=8.8 Hz, 1H), 7.5 (dd, J=2.5 and 8.8 Hz, 1H), 5.8 (s, 1H), 4.1 (t, J=6 Hz, 2H), 3.75-3.15 (m, 10H), 2.8 (s, 3H), 2.3 (s, 3H), 1.8-1.7 (m, 4H).

Example 26

1-{4-[1-(3,4-Dichlorophenyl)-5-methyl-1H-pyrazol-3-yloxy]butyl}-1H-imidazole

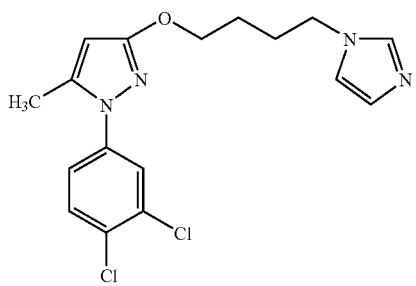 [SMILES: Cc1cc(OCCCCn2ccnc2)nn1-c1ccc(Cl)c(Cl)c1]

Oil. Yield=30%
$^1$H-1-NMR (CDCl$_3$) δ ppm: 7.6 (s, 1H), 7.55 (d, J=2.3 Hz, 1H), 7.5 (d, J=8.7 Hz, 1H), 7.3 (dd, J=2.3 and 8.7 Hz, 1H), 7.1 (s, 1H), 6.95 (s, 1H), 5.65 (s, 1H), 4.2 (t, J=6.2 Hz, 2H), 4.05 (t, J=7.2 Hz, 2H), 2.3 (s, 3H), 2.0 (m, 2H), 1.8 (m, 2H).

Example 27

4-[1-(3,4-Dichlorophenyl)-5-methyl-1H-pyrazol-3-yloxy]-N,N-diethylbutan-1-amine

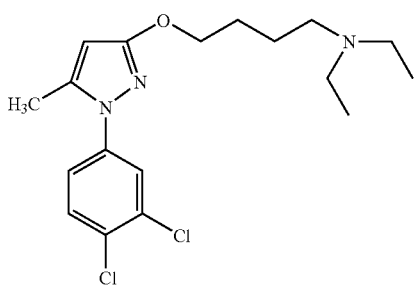 [SMILES: CCN(CC)CCCCOc1cc(C)n(-c2ccc(Cl)c(Cl)c2)n1]

Oil. Yield=39%.
$^1$H-NMR (CDCl$_3$) δ ppm: 7.5 (d, J=2.5 Hz, 1H), 7.4 (d, J=8.6 Hz, 1H), 7.2 (dd, J=2.5 and 8.6 Hz, 1H), 5.6 (s, 1H), 4.1 (t, J=6.2 Hz, 2H), 2.5 (m, 6H), 2.25 (s, 3H), 1.7-1.55 (m, 4H), 1.0 (t, J=6.4 Hz, 6H).

Example 28

1-{4-[1-(3,4-dichlorophenyl)-5-methyl-1H-pyrazol-3-yloxy]butyl}-4-phenylpiperidine hydrochloride

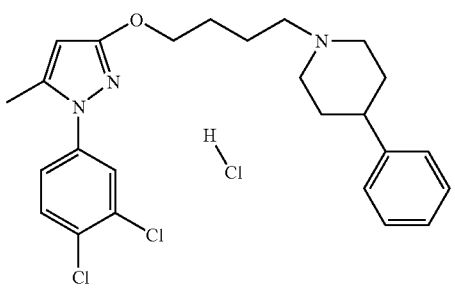 [SMILES: Cc1cc(OCCCCN2CCC(c3ccccc3)CC2)nn1-c1ccc(Cl)c(Cl)c1 ; Cl]

White solid. M.p.=166-170° C. Yield=37%
$^1$H-NMR (DMSO-d$_6$) δ ppm: 9.8 (br s, 1H), 7.8 (d, J=2.4 Hz, 1H), 7.7 (d, J=8.8 Hz, 1H), 7.5 (dd, J=2.4 and 8.8 Hz, 1H), 7.35-7.2 (m, 5H), 5.8 (s, 1H), 4.1 (t, J=5.8 Hz, 2H), 3.5 (d, J=11.6 Hz, 2H), 3.1-3.0 (m, 4H), 2.8 (m, 1H), 2.3 (s, 3H), 2.0-1.75 (m, 8H).

Example 29

1-{4-[1-(3,4-dichlorophenyl)-5-methyl-1H-pyrazol-3-yloxy]butyl}-6,7-dihydro-1H-indol-4(5H)-one

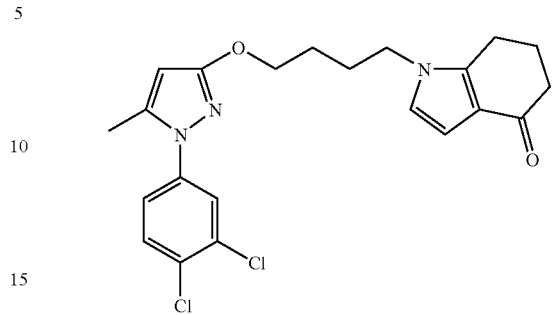

Oil. Yield=13%
$^1$H-NMR (CDCl$_3$) δ ppm: 7.55 (d, J=2.3 Hz, 1H), 7.5 (d, J=8.7 Hz, 1H), 7.25 (dd+solvent, J=2.3 and 8.7 Hz, 1H), 6.6 (d, J=2.9 Hz, 1H), 6.55 (d, J=2.2 Hz, 1H), 5.6 (s, 1H), 4.2 (t, J=6.0 Hz, 2H), 3.9 (t, J=7.0 Hz, 2H), 2.75 (t, J=6.2 Hz, 2H), 2.45 (t, J=6.4 Hz, 2H), 2.3 (s, 3H), 2.15 (m, 2H), 1.9-1.7 (m, 4H).

Example 30

2-{4-[1-(3,4-dichlorophenyl)-5-methyl-1H-pyrazol-3-yloxy]butyl}-1,2,3,4-tetrahydroisoquinoline

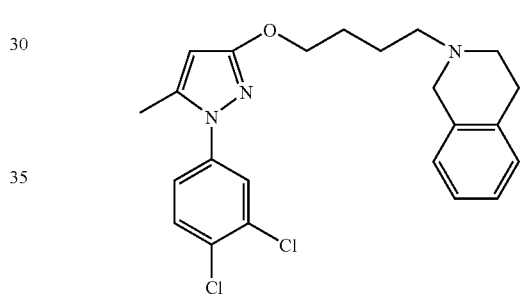

Oil. Yield=61%
$^1$H-NMR (CDCl$_3$) δ ppm: 7.5 (d, J=2.2 Hz, 1H), 7.4 (d, J=8.7 Hz, 1H), 7.2 (dd+solvent, J=2.2 and 8.7 Hz, 1H), 7.05 (m, 3H), 6.95 (m, 1H), 5.6 (s, 1H), 4.2 (m, 2H), 3.6 (m, 2H), 2.9-2.7 (m, 4H), 2.6 (m, 2H), 2.25 (s, 3H), 1.8 (m, 4H).

Example 31

4-{2-[1-(3,4-dichlorophenyl)-5-isopropyl-1H-pyrazol-3-yloxy]ethyl}morpholine hydrochloride

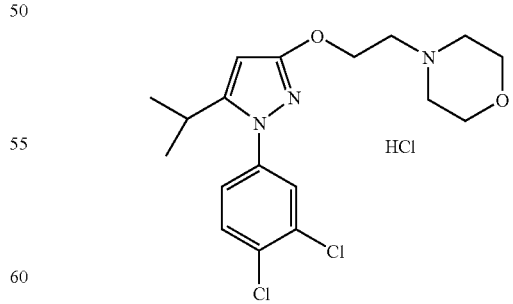

White solid. M.p.=195-197° C. Yield=47%
$^1$H-NMR (DMSO-d$_6$) δ ppm: 10.5 (br s, 1H), 7.75 (2 d, J=2.5 and 8.6 Hz, 2H), 7.45 (dd, J=2.5 and 8.6 Hz, 1H), 5.9 (s, 1H), 4.5 (bs, 2H), 3.95 (m, 2H), 3.75 (t, J=11.7 Hz, 2H), 3.5 (m, 4H), 3.15 (m, 2H), 3.0 (sep, J=6.9 Hz, 1H), 1.1 (d, J=6.9 Hz, 6H).

Example 32

2-[1-(3,4-Dichlorophenyl)-5-isopropyl-1H-pyrazol-3-yloxy]-N,N-diethylethanamine

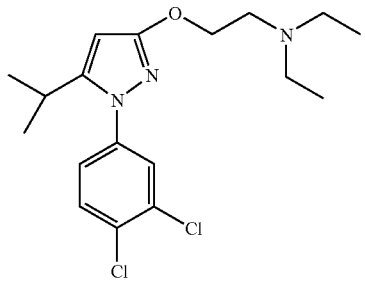 [SMILES: CCN(CC)CCOc1cc(C(C)C)n(-c2ccc(Cl)c(Cl)c2)n1]

Oil. Yield=32%
$^1$H-NMR (CDCl$_3$) δ ppm: 7.55 (d, J=2.3 Hz, 1H), 7.5 (d, J=8.6 Hz, 1H), 7.25 (dd, J=2.3 and 8.6 Hz, 1H), 5.7 (s, 1H), 4.3 (t, J=5.8 Hz, 2H), 3.0 (m, 3H), 2.7 (m, 4H), 1.2 (d, J=6.9 Hz, 6H), 1.1 (t, J=7.1 Hz, 6H)

Example 33

1-(3,4-Dichlorophenyl)-5-isopropyl-3-[2-(pyrrolidin-1-yl)ethoxy]-1H-pyrazole hydrochloride

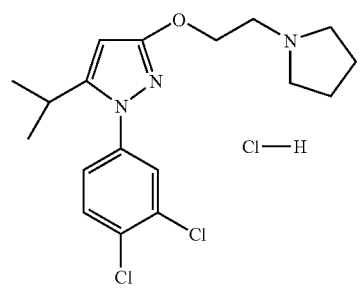

White solid. M.p.=138-142° C. Yield=17%
$^1$H-NMR (DMSO-d$_6$) δ ppm: 10.15 (br s, 1H), 7.8 (m, 2H), 7.45 (dd, J=2.4 and 8.7 Hz, 1H), 5.9 (s, 1H), 4.4 (t, J=4.6 Hz, 2H), 3.5 (m, 4H), 3.05 (m, 3H), 2.0-1.8 (m, 4H), 1.1 (d, J=6.7 Hz, 6H).

Example 34

1-(3,4-Dichlorophenyl)-5-isopropyl-3-[3-(pyrrolidin-1-yl)propoxy]-1H-pyrazole hydrochloride

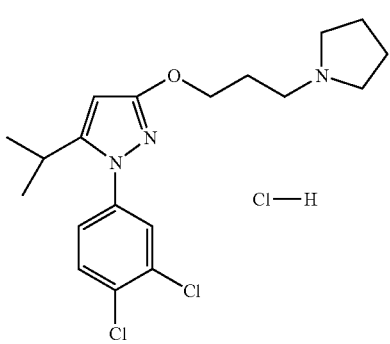 [SMILES: CC(C)c1cc(OCCCN2CCCC2)nn1-c1ccc(Cl)c(Cl)c1 ; Cl]

White solid. M.p.=152-156° C. Yield=29%
$^1$H-NMR (DMSO-d$_6$) δ ppm: 10.2 (br s, 1H), 7.75 (m, 2H), 7.45 (dd, J=2.4 and 8.7 Hz, 1H), 5.85 (s, 1H), 4.15 (t, J=6.0 Hz, 2H), 3.5 (m, 2H), 3.2 (m, 2H), 3.0 (m, 3H), 2.1-1.8 (m, 6H), 1.1 (d, J=6.7 Hz, 6H).

Example 35

1-{2-[1-(3,4-Dichlorophenyl)-5-isopropyl-4H-pyrazol-3-yloxy]ethyl}piperidine

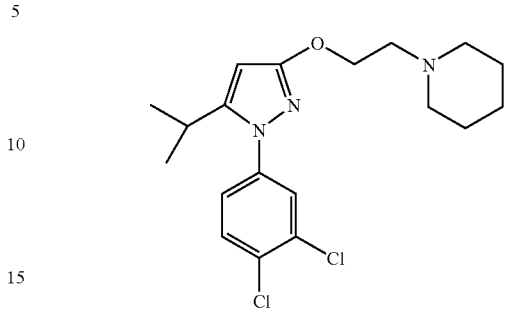

Oil. Yield=42%
$^1$H-NMR (CDCl$_3$) δ ppm: 7.5 (d, J=2.4 Hz, 1H), 7.45 (d, J=8.6 Hz, 1H), 7.3 (m, 1H), 5.7 (s, 1H), 4.3 (t, J=5.7 Hz, 2H), 2.95 (sep, J=6.7 Hz, 1H), 2.8 (m, 2H), 2.5 (m, 4H), 1.6 (m, 4H), 1.45 (m, 2H), 1.15 (d, J=6.7 Hz, 6H).

Example 36

2-{2-[1-(3,4-dichlorophenyl)-5-isopropyl-1H-pyrazol-3-yloxy]ethyl}-1,2,3,4-tetrahydroisoquinoline hydrochloride

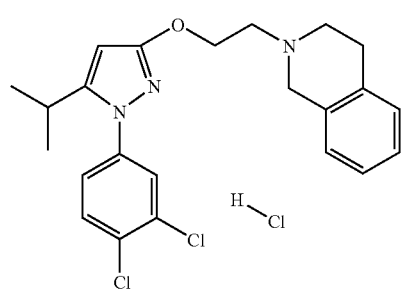

White solid. M.p.=186-191° C. Yield=33%.
$^1$H-NMR (CDCl$_3$) δ ppm: 13.4 (bs, 1H), 7.55 (d, J=8.6 Hz, 1H), 7.5 (d, J=2.3 Hz, 1H), 7.3-7.15 (m, 4H), 7.1 (d, J=7.0 Hz, 1H), 5.7 (s, 1H), 4.8 (t, J=4.4 Hz, 2H), 4.65 (dd, J=12.8 and 3 Hz, 1H), 4.25 (dd, J=5.5 and 15.8 Hz, 1H), 3.8-3.7 (m, 1H), 3.6-3.4 (m, 4H), 3.15-3.05 (m, 1H), 2.95 (sep, J=6.7 Hz, 1H), 1.2 (d, J=6.7 Hz, 6H).

Example 37

Synthesis of 4-{2-[1-(3,4-dichlorophenyl)-1H-pyrazol-3-yloxy]ethyl}morpholine Scheme I, step 1: Synthesis of 1-(3,4-dichlorophenyl)-1H-pyrazol-3-ol

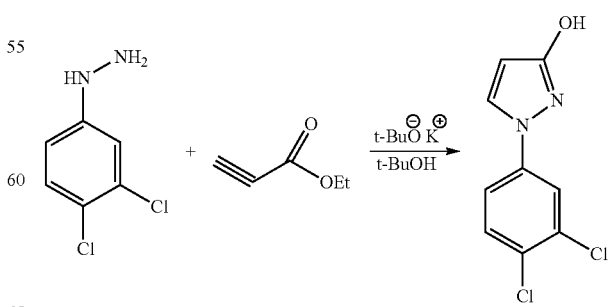

N'-(3,4-Dichlorophenyl)hydrazine was liberated from its hydrochloride (8.7 g, 40.6 mmol) by partitioning the solid between dilutes Na₂CO₃ solution and ethyl acetate. The aqueous layer was extracted 2 more times with AcOEt, dried over Na₂SO₄ and the solvent removed in vacuo. The residue is taken up in t-butyl alcohol (60 ml) and, in a dry nitrogen atmosphere, the ethyle propionate (4.6 ml, 44.66 mmol) was dropwise added. The mixture was ice-cooled and potassium t-butoxide (10.5 g, 81.2 mmol) was slowly added over the time of 1 hr. The resulting mixture was stirred overnight at room temperature. The solvent was evaporated in vacuo and ice-water was added. The resulting aqueous solution is extracted with dichloromethane and acidified to pH 6 with acetic acid. The solid precipitated was filtered off, dried and crystallized from ethyl acetate yielding 2.4 g of brown solid. The mother liquors were evaporated to dryness and the crude residue was column chromatographied on silica gel (petroleum ether/AcOEt 9:1) another fraction of 1 g was obtained (total yield 37%)

¹H-NMR (CDCl₃) δ ppm: 7.65 (d, J=2.7 Hz, 1H), 7.6 (d, J=2.5 Hz, 1H), 7.5 (d, J=8.8 Hz, 1H), 7.35 (dd, J=2.5 and 8.8 Hz, 1H), 5.95 (d, J=2.7 Hz, 1H).

Synthesis of 4-{2-[1-(3,4-dichlorophenyl)-1H-pyrazol-3-yloxy]ethyl}morpholine (Scheme I, step 2B.)

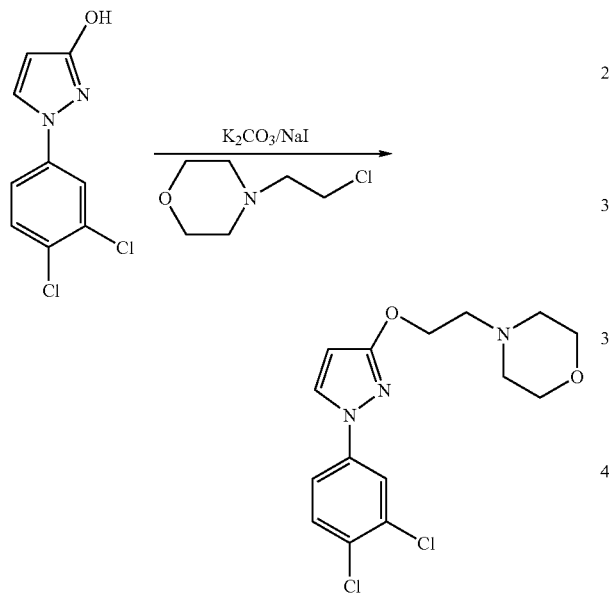

The compound was obtained starting from 1-(3,4-dichlorophenyl)-1H-pyrazol-3-ol and N-(2-chloroethyl)morpholine hydrochloride using the same synthetic procedure described in Step 3 of Example 1.

Thus 4-{2-[1-(3,4-dichlorophenyl)-1H-pyrazol-3-yloxy]ethyl}morpholine

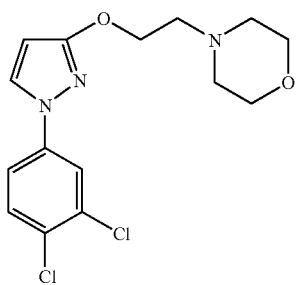 [SMILES: Clc1ccc(-n2ccc(OCCN3CCOCC3)n2)cc1Cl]

Oil. Yield=78%
¹H-NMR (CDCl₃) δ ppm: 7.7 (d, J=2.4 Hz, 1H), 7.65 (d, J=2.7 Hz, 1H), 7.4 (m, 2H), 5.95 (d, J=2.7 Hz, 1H), 4.4 (m, 2H), 3.75 (m, 4H), 2.8 (m, 2H), 2.6 (m, 4H).
Hydrochloride salt: white solid. M.p.=162-166° C.

Example 38

2-[1-(3,4-dichlorophenyl)-1H-pyrazol-3-yloxy]N,N-diethylethanamine

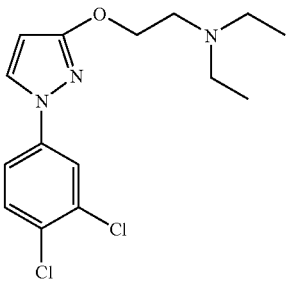 [SMILES: CCN(CC)CCOc1ccn(-c2ccc(Cl)c(Cl)c2)n1]

Oil. Yield=53%
¹H-NMR (CDCl₃) δ ppm: 7.75 (d, J=2.2 Hz, 1H), 7.65 (d, J=2.7 Hz, 1H), 7.4 (m, 2H), 5.9 (d, J=2.7 Hz, 1H), 4.3 (t, J=6.2 Hz, 2H), 2.9 (t, J=6.2 Hz, 2H), 2.65 (q, J=7.1 Hz, 4H), 1.1 (t, J=7.1 Hz, 6H).
Hydrochloride salt: white solid. M.p.=142-151° C.

Example 39

1-(3,4-dichlorophenyl)-3-[2-(pyrrolidin-1-yl)ethoxy]-1H-pyrazole

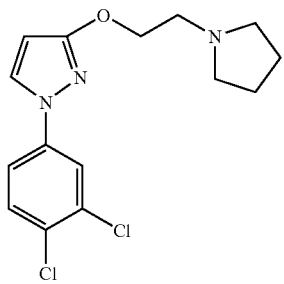 [SMILES: Clc1ccc(-n2ccc(OCCN3CCCC3)n2)cc1Cl]

Oil. Yield=45%
¹H-NMR (CDCl₃) δ ppm: 7.7 (d, J=2.0 Hz, 1H), 7.65 (d, J=2.8 Hz, 1H), 7.4 (m, 2H), 5.95 (d, J=2.7 Hz, 1H), 4.4 (t, J=5.8 Hz, 2H), 2.9 (t, J=5.8 Hz, 2H), 2.65 (m, 4H), 1.8 (m, 4H).
Hydrochloride salt: White solid. M.p.=172-176° C.

Example 40

1-{2-[1-(3,4-dichlorophenyl)-1H-pyrazol-3-yloxy]ethyl}piperidine

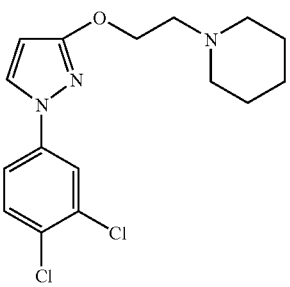 [SMILES: Clc1ccc(-n2ccc(OCCN3CCCCC3)n2)cc1Cl]

Oil. Yield=57%
¹H-NMR (CDCl₃) δ ppm: 7.75 (d, J=2.1 Hz, 1H), 7.65 (d, J=2.6 Hz, 1H), 7.4 (m, 2H), 5.9 (d, J=2.5 Hz, 1H), 4.4 (t, J=5.5 Hz, 2H), 2.8 (m, 2H), 2.5 (m, 4H), 1.7-1.4 (m, 6H).
Hydrochloride salt: white solid. M.p.=172-177° C.

Example 41

1-(3,4-dichlorophenyl)-3-[3-(pyrrolidin-1-yl)propoxy]-1H-pyrazole

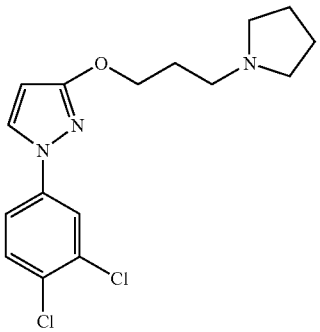 [SMILES: Clc1ccc(-n2ccc(OCCCN3CCCC3)n2)cc1Cl]

Oil. Yield=51%
<sup>1</sup>H-NMR (CDCl<sub>3</sub>) δ ppm: 7.7 (d, J=2.1 Hz, 1H), 7.6 (d, J=2.6 Hz, 1H), 7.35 (m, 2H), 5.85 (d, J=2.6 Hz, 1H), 4.2 (t, J=6.3 Hz, 2H), 2.65 (t, J=7.6 Hz, 2H), 2.55 (m, 4H), 2.05-1.75 (m, 6H).
Hydrochloride salt: beige colour solid. M.p.=156-159° C.
<sup>1</sup>H-NMR (CDCl<sub>3</sub>) δ ppm: 12.7 (bs, 1H), 7.7 (2d, J=2.5 and 2.6 Hz, 2H), 7.5-7.4 (m, 2H), 5.9 (d, J=2.6 Hz, 1H), 4.35 (t, J=5.7 Hz, 2H), 3.8 (m, 2H), 3.3 (m, 2H), 2.8 (m, 2H), 2.45 (m, 2H), 2.25 (m, 2H), 2.05 (m, 2H).

Example 42

1-{2-[1-(3,4-Dichlorophenyl)-5-methyl-1H-pyrazol-3-yloxy]ethyl}piperazine dihydrochloride

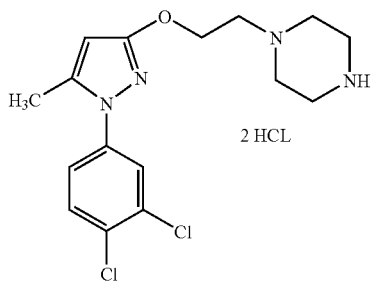 [SMILES: Cc1cc(OCCN2CCNCC2)nn1-c1ccc(Cl)c(Cl)c1]

White solid. Yield=60%
<sup>1</sup>H-NMR (DMSO-d<sub>6</sub>+TFAA) δ ppm: 9.1 (br s, 1H), 7.7 (d, J=2.3 Hz, 1H), 7.6 (d, 3=8.7 Hz, 1H), 7.4 (dd, 3=2.3 and 8.7 Hz, 1H), 5.8 (s, 1H), 4.45 (m, 2H), 3.6-3.2 (m, 10H), 2.3 (s, 3H).

Example 43

1-{2-[1-(3,4-Dichlorophenyl)-5-methyl-1H-pyrazol-3-yloxy]ethyl}pyrrolidin-3-amine

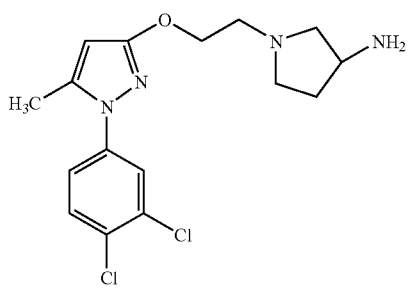 [SMILES: Cc1cc(OCCN2CCC(N)C2)nn1-c1ccc(Cl)c(Cl)c1]

Oil. Yield=45%
<sup>1</sup>H-NMR (DMSO-d<sub>6</sub>) δ ppm: 7.75 (d, J=2.5 Hz, 1H), 7.7 (d, J=8.7 Hz, 1H), 7.5 (dd, J=2.5 and 8.7 Hz, 1H), 5.8 (s, 1H), 4.15 (t, J=5.7 Hz, 2H), 2.7 (t, J=5.7 Hz, 2H), 2.65-2.5 (m, 4H), 2.3 (s, 3H), 2.2 (m, 1H), 1.95 (m, 1H), 1.35 (m, 1H).

Example 44

4-(2-(1-(3,4-Dichlorophenyl)-4,5-dimethyl-1H-pyrazol-3-yloxy)ethyl)morpholine

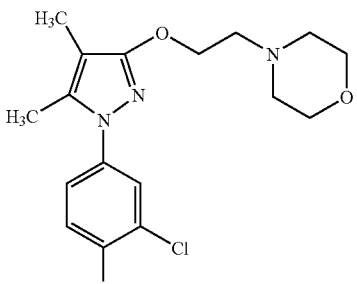

Oil. Yield=76%
<sup>1</sup>H-NMR (DMSO-d<sub>6</sub>) δ ppm: 7.7 (d, J=2.5 Hz, 1H), 7.65 (d, J=8.8 Hz, 1H), 7.45 (dd, J=2.5 and 8.8 Hz, 1H), 4.25 (t, J=5.7 Hz, 2H), 3.55 (t, J=4.7 Hz, 4H), 2.65 (t, J=5.7 Hz, 2H), 2.4 (t, J=4.7 Hz, 4H), 2.25 (s, 3H), 1.8 (s, 3H).
Hydrochloride salt: white solid. M.p. 175-179° C.

Example 45

2-(1-(3,4-Dichlorophenyl)-4,5-dimethyl-1H-pyrazol-3-yloxy)-N,N-diethylethanamine hydrochloride

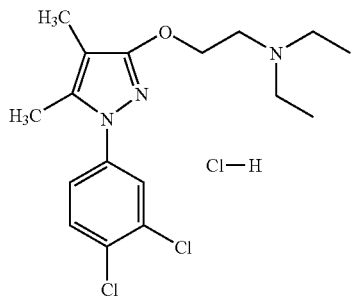 [SMILES: CCN(CC)CCOc1nn(-c2ccc(Cl)c(Cl)c2)c(C)c1C ; Cl]

White solid. Yield=40%. M.p.=134-136° C.
<sup>1</sup>H-NMR (DMSO-d<sub>6</sub>+TFAA) δ ppm: 9.4 (br s, 1H), 7.65 (d, J=2.5 Hz, 1H), 7.6 (d, J=8.7 Hz, 1H), 7.4 (dd, 3=2.5 and 8.7 Hz, 1H), 4.45 (t, 3=5.0 Hz, 2H), 3.5 (m, 2H), 3.15 (m, 4H), 2.2 (s, 3H), 1.8 (s, 3H), 1.2 (t, J=7.0 Hz, 6H).

Example 46

1-(3,4-dichlorophenyl)-4,5-dimethyl-3-(2-(pyrrolidin-1-yl)ethoxy)-1H-pyrazole hydrochloride

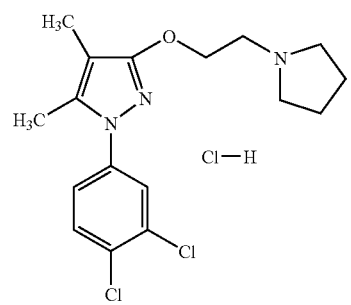 [SMILES: Cc1c(OCCN2CCCC2)nn(-c2ccc(Cl)c(Cl)c2)c1C ; Cl]

Beige solid. Yield=31%. M.p.=146-148° C.
¹H-NMR (DMSO-d₆) δ ppm: 10.3 (br s, 1H), 7.75 (d, J=2.5 Hz, 1H), 7.7 (d, J=8.8 Hz, 1H), 7.5 (dd, J=2.5 and 8.8 Hz, 1H), 4.5 (t, J=4.8 Hz, 2H), 3.55 (m, 4H), 3.15-3.05 (m, 2H), 2.25 (s, 3H), 2.05-1.95 (m, 2H), 1.85 (s+m, 5H).

Example 47

1-(3,4-dichlorophenyl)-4,5-dimethyl-3-(3-(pyrrolidin-1-yl)propoxy)-1H-pyrazole hydrochloride

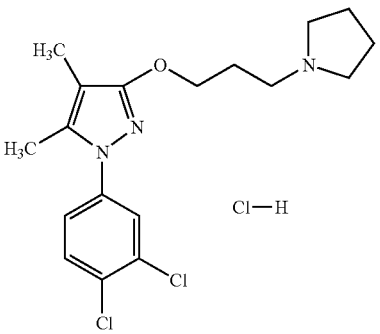 [SMILES: Cc1c(OCCCN2CCCC2)nn(-c2ccc(Cl)c(Cl)c2)c1C ; Cl]

Beige solid. Yield=63%. M.p.=155-157° C.
¹H-NMR (DMSO-d₆+TFAA) δ ppm: 9.5 (br s, 1H), 7.6 (d, J=2.5 Hz, 1H), 7.55 (d, J=8.7 Hz, 1H), 7.35 (dd, J=2.5 and 8.7 Hz, 1H), 4.2 (t, J=5.8 Hz, 2H), 3.5 (m, 2H), 3.2 (m, 2H), 2.9 (m, 2H), 2.15 (s, 3H), 2.1 (m, 2H), 1.9 (m, 2H), 1.85-1.75 (m+s, 5H).

Example 48

1-(2-(1-(3,4-Dichlorophenyl)-4,5-dimethyl-1H-pyrazol-3-yloxy)ethyl)piperidine

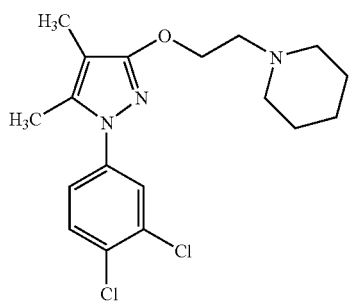 [SMILES: Cc1c(OCCN2CCCCC2)nn(-c2ccc(Cl)c(Cl)c2)c1C]

Beige solid. MP 64-67° C.
¹H-NMR (DMSO-d₆) δ ppm: 7.75 (d, J=2.4 Hz, 1H), 7.7 (d, J=8.8 Hz, 1H), 7.45 (dd, J=2.4 and 8.8 Hz, 1H), 4.25 (t, J=5.6 Hz, 2H), 2.65 (m, 2H), 2.4 (m, 4H), 2.25 (s, 3H), 1.8 (s, 3H), 1.5-1.35 (m, 6H).

Example 49

4-{4-[1-(3,4-dichlorophenyl)-1H-pyrazol-3-yloxy]butyl}morpholine hydrochloride

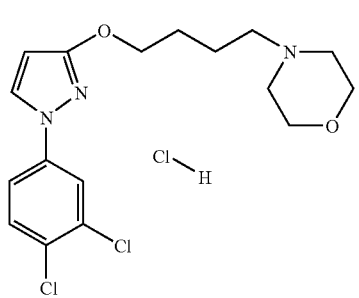 [SMILES: Clc1ccc(-n2ccc(OCCCCN3CCOCC3)n2)cc1Cl ; Cl]

White solid. M.p.=165-169° C. Yield=66%
¹H-NMR (CDCl₃) δ ppm: 13.1 (br s, 1H), 7.75 (d, J=2.4 Hz, 1H), 7.7 (d, J=2.6 Hz, 1H), 7.5 (d, J=8.8 Hz, 1H), 7.4 (dd, J=2.4 and 8.8 Hz, 1H), 5.9 (d, J=2.6 Hz, 1H), 4.3 (m, 4H), 4.0 (m, 2H), 3.45 (m, 2H), 3.05 (m, 2H), 2.9-2.8 (m, 2H), 2.15 (m, 2H), 1.9 (m, 2H).

Example 50

(2S,6R)-4-{4-[1-(3,4-dichlorophenyl)-1H-pyrazol-3-yloxy]butyl}-2,6-dimethylmorpholine hydrochloride

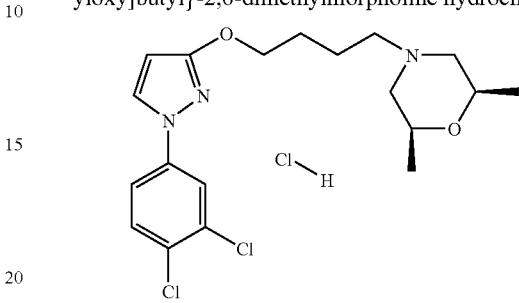

White solid. M.p.=149-154° C. Yield=36%
¹H-NMR (CDCl₃) δ ppm: 13.0 (br s, 1H), 7.75 (d, J=2.3 Hz, 1H), 7.7 (d, J=2.6 Hz, 1H), 7.5-7.4 (m, 2H), 5.9 (d, J=2.6 Hz, 1H), 4.4 (m, 2H), 4.3 (t, 0.1-5.8 Hz, 2H), 3.35 (d, J=11.5 Hz, 2H), 3.05 (m, 2H), 2.35 (q, J=10.8 Hz, 2H), 2.15 (m, 2H), 1.9 (m, 2H), 1.2 (d, J=6.3 Hz, 6H).

Example 51

1-{4-[1-(3,4-Dichlorophenyl)-1H-pyrazol-3-yloxy]butyl}piperidine hydrochloride

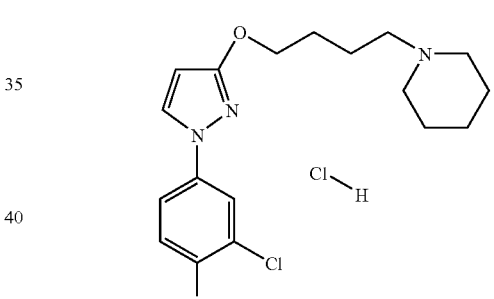

White solid. m.p.=156-161° C. Yield=25%
¹H-NMR (CDCl₃) δ ppm: 12.2 (br s, 1H), 7.75 (d, J=2.4 Hz, 1H), 7.7 (d, J=2.6 Hz, 1H), 7.5-7.4 (m, 2H), 5.9 (d, J=2.6 Hz, 1H), 4.3 (t, J=5.8 Hz, 2H), 3.55 (d, J=11 Hz, 2H), 3.0 (m, 2H), 2.6 (q, J=9.5 Hz, 2H), 2.35 (q, J=12.6 Hz, 2H), 2.15 (m, 2H), 1.9-1.8 (m, 5H), 1.4 (m, 1H).

Example 52

1-(3,4-Dichlorophenyl)-3-(4-[pyrrolidin-1-yl]butoxy)-1H-pyrazole hydrochloride

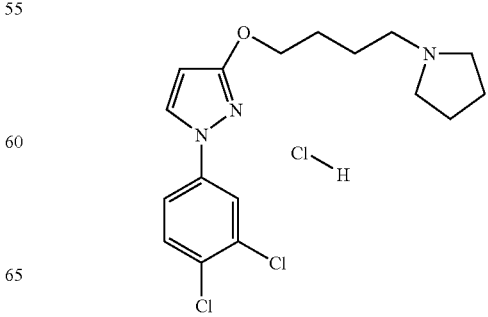

White solid. M.p.=181-186° C. Yield=30%

$^1$H-NMR (CDCl$_3$) δ ppm: 12.4 (br s, 1H), 7.75 (d, J=2.4 Hz, 1H), 7.7 (d, J=2.6 Hz, 1H), 7.5-7.4 (m, 2H), 5.9 (d, J=2.6 Hz, 1H), 4.25 (t, J=5.9 Hz, 2H), 3.8 (m, 2H), 3.1 (m, 2H), 2.8 (m, 2H), 2.3-1.9 (m, 8H).

Example 53

4-[1-(3,4-dichlorophenyl)-1H-pyrazol-3-yloxy]-N,N-diethylbutan-1-amine oxalate

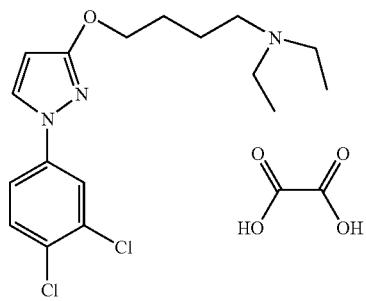

White solid. M.p.=130-135° C. Yield=22%

$^1$H-NMR (CD$_3$OD) δ ppm: 8.1 (d, J=2.5 Hz, 1H), 7.9 (d, J=2.2 Hz, 1H), 7.6 (m, 2H), 6.0 (d, J=2.4 Hz, 1H), 4.35 (m, 2H), 3.25 (q, J=7.1 Hz, 6H), 1.9 (m, 4H), 1.35 (t, J=7.1 Hz, 6H).

Example 54

N-benzyl-4-[1-(3,4-dichlorophenyl)-1H-pyrazol-3-yloxy]-N-methylbutan-1-amine oxalate

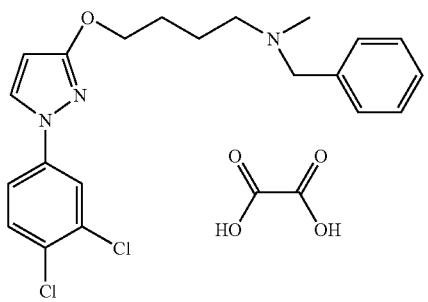

White solid. M.p.=141-143° C. Yield=37%

$^1$H-NMR (CD$_3$OD) δ ppm: 8.1 (d, J=2.6 Hz, 1H), 7.9 (d, J=2.4 Hz, 1H), 7.6 (m, 2H), 7.5 (m, 5H), 6.0 (d, J=2.6 Hz, 1H), 4.35 (s, 2H), 4.3 (t, J=5.7 Hz, 2H), 3.25 (m, 2H), 2.8 (s, 3H), 1.9 (m, 4H).

Example 55

4-[1-(3,4-dichlorophenyl)-1H-pyrazol-3-yloxy]-N-(2-methoxyethyl)-N-methylbutan-1-amine oxalate

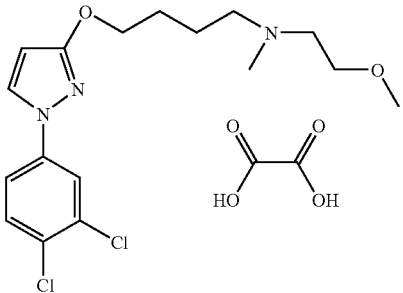

White solid. Yield=56%. M.p.=97-100° C.

$^1$H-NMR (CD$_3$OD) δ ppm: 8.1 (d, J=2.6 Hz, 1H), 7.9 (d, J=2.2 Hz, 1H), 7.6 (m, 2H), 6.0 (d, J=2.6 Hz, 1H), 4.35 (t, J=5.7 Hz, 2H), 3.7 (t, J=5.0 Hz, 2H), 3.4 (s, 3H), 3.4-3.2 (m, 4H), 2.9 (s, 3H), 1.9 (m, 4H).

Example 56

4-{4-[1-(3,4-dichlorophenyl)-1H-pyrazol-3-yloxy]butyl}thiomorpholine oxalate

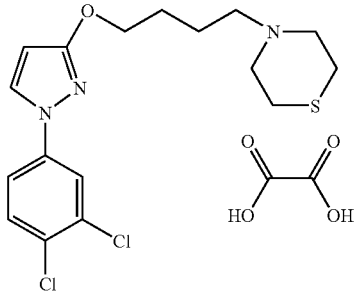

White solid. Yield=66%. M.p.=175-177° C.

$^1$H-NMR (DMSO-d$_6$) δ ppm: 8.4 (d, J=2.7 Hz, 1H), 8.0 (d, J=2.2 Hz, 1H), 7.7 (m, 2H), 6.05 (d, J=2.6 Hz, 1H), 4.2 (m, 2H), 3.1 (m, 4H), 2.85-2.75 (m, 6H), 1.7 (m, 4H).

Example 57

1-[1-(3,4-Dichlorophenyl)-5-methyl-3-(2-morpholinoethoxy)-1H-pyrazol-4-yl]ethanone oxalate

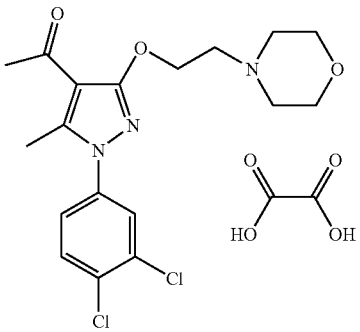

White solid. Yield=74%. M.p.=188-192° C.

$^1$H-NMR (DMSO-d$_6$) δ ppm: 7.85 (d, J=2.5 Hz, 1H), 7.8 (d, J=8.6 Hz, 1H), 7.55 (dd, J=2.5 and 8.6 Hz, 1H), 4.35 (m, 2H), 3.6 (m, 4H), 2.9 (m, 2H), 2.65 (m, 4H), 2.5 (s, 3H), 2.4 (s, 3H).

Example 58

1-{1-(3,4-dichlorophenyl)-5-methyl-3-[2-(pyrrolidin-1-yl)ethoxy]-1H-pyrazol-4-yl}ethanone oxalate

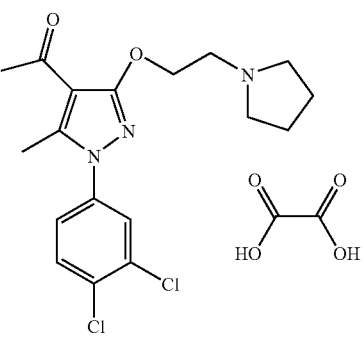

White solid. Yield=58%. M.p.=159-162° C.
$^1$H-NMR (CD$_3$OD) δ ppm: 7.75 (2d, J=1.6 y 8.5 Hz, 2H), 7.45 (dd, J=1.6 y 8.5 Hz, 1H), 4.65 (t, J=5.0 Hz 2H), 3.65 (t, J=5.0 Hz, 2H), 3.5 (m, 4H), 2.55 (s, 3H), 2.50 (s, 3H), 2.15 (m, 4H).

Example 59

1-{1-(3,4-dichlorophenyl)-5-methyl-3-[2-(piperidin-1-yl)ethoxy]-1H-pyrazol-4-yl}ethanone oxalate

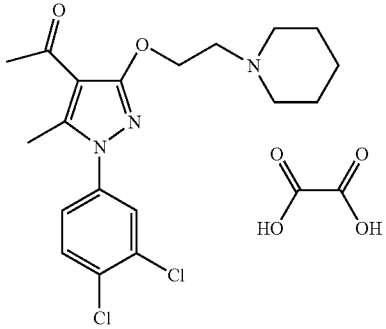

White solid. Yield=81%. M.p.=158-161° C.
$^1$H-NMR (DMSO-d$_6$) δ ppm: 7.85 (d, J=2.3 Hz, 1H), 7.8 (d, J=8.6 Hz, 1H), 7.55 (dd, J=2.3 and 8.6 Hz, 1H), 4.5 (m, 2H), 3.25 (m, 2H), 3.0 (m, 4H), 2.5 (s, 3H), 2.4 (s, 3H), 1.7 (m, 4H), 1.5 (m, 2H).

Example 60

1-{1-(3,4-dichlorophenyl)-3-[2-(diethylamino)ethoxy]-5-methyl-1H-pyrazol-4-yl}ethanone oxalate

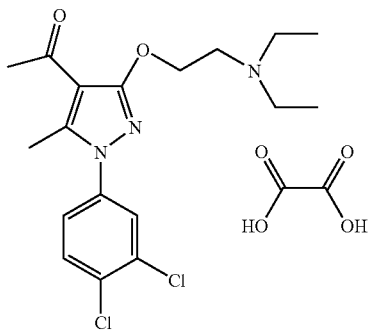

White solid. Yield=75%. M.p.=147-149° C.
$^1$H-NMR (DMSO-d$_6$) δ ppm: 7.85 (d, J=2.3 Hz, 1H), 7.8 (d, J=8.6 Hz, 1H), 7.55 (dd, J=2.3 and 8.6 Hz, 1H), 4.45 (t, J=5.2 Hz, 2H), 3.3 (m, 2H), 3.0 (q, J=8.0 Hz, 4H), 2.5 (s, 3H), 2.4 (s, 3H), 1.15 (t, J=8.0 Hz, 6H).

Example 61

4-{2-[5-Methyl-1-(naphthalen-2-yl)-1H-pyrazol-3-yloxy]ethyl}morpholine

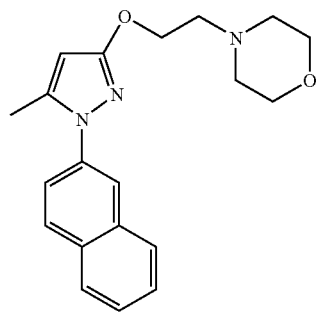 [SMILES: Cc1cc(OCCN2CCOCC2)nn1-c1ccc2ccccc2c1]

Oil. Yield=45%
$^1$H-NMR (CDCl$_3$) δ ppm: 7.9-7.8 (m, 4H), 7.6-7.5 (m, 3H), 5.7 (s, 1H), 4.4 (m, 2H), 3.8 (m, 4H), 2.85 (m, 2H), 2.65 (m, 4H), 2.35 (s, 3H).

Example 62

N,N-Diethyl-2-[5-methyl-1-(naphthalen-2-yl)-1H-pyrazol-3-yloxy]ethanamine

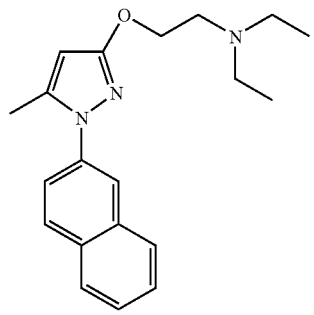 [SMILES: CCN(CC)CCOc1cc(C)n(-c2ccc3ccccc3c2)n1]

Oil. Yield=27%
$^1$H-NMR (CDCl$_3$) δ ppm: 8.0-7.8 (m, 4H), 7.6-7.5 (m, 3H), 5.7 (s, 1H), 4.4 (m, 2H), 3.05 (m, 2H), 2.8 (m, 4H), 2.35 (s, 3H), 1.2 (m, 6H).

Example 63

1-{2-[5-Methyl-1-(naphthalen-2-yl)-1H-pyrazol-3-yloxy]ethyl}piperidine hydrochloride

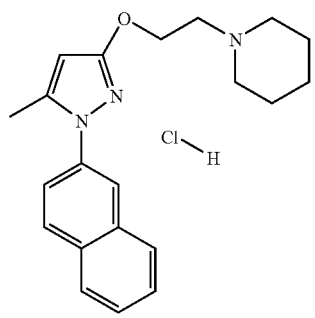 [SMILES: Cc1cc(OCCN2CCCCC2)nn1-c1ccc2ccccc2c1 ; Cl]

White solid. Yield=29.4% m.p.=198-202° C.
$^1$H-NMR (CDCl$_3$) δ ppm: 12.4 (bs, 1H), 8.0-7.8 (m, 4H), 7.6-7.5 (m, 3H), 5.7 (s, 1H), 4.75 (t, J=4.3 Hz, 2H), 3.6 (d, J=11.9 Hz, 2H), 3.4 (m, 2H), 2.8 (q, J=10.0 Hz, 2H), 2.35-2.2 (m+s, 5H), 1.85 (m, 3H), 1.4 (m, 1H).

Example 64

5-Methyl-1-(naphthalen-2-yl)-3-[2-(pyrrolidin-1-yl)ethoxy]-1H-pyrazole hydrochloride

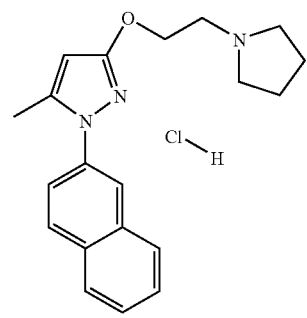 [SMILES: Cc1cc(OCCN2CCCC2)nn1-c1ccc2ccccc2c1 ; Cl]

White solid. Yield=10% m.p.=170-171° C.

$^1$H-NMR (CDCl$_3$) δ ppm: 12.8 (bs, 1H), 7.95-7.8 (m, 4H), 7.6-7.5 (m, 3H), 5.75 (s, 1H), 4.75 (t, J=4.5 Hz, 2H), 3.9 (m, 2H), 3.5 (m, 2H), 3.0 (m, 2H), 2.35 (s, 3H), 2.2 (m, 2H), 2.05 (m, 2H).

Biological Activity

Some representative compounds of the invention were tested for their activity as sigma (sigma-1 and sigma-2) inhibitors. The following protocols were followed:

Sigma-1

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 mM at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 μM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

DeHaven-Hudkins, D. L., L. C. Fleissner, and F. Y. Ford-Rice, 1992, "Characterization of the binding of [$^3$H](+)pentazocine to a recognition sites in guinea pig brain", *Eur. J. Pharmacol.* 227, 371-378.

Lowry, O. H., N. J. Rosebrough, A. L. Farr, and R. J. Randall, 1951, Protein measurement with the Folin phenol reagent, *J. Biol. Chem*, 193, 265.

Sigma-2

Binding studies for σ2-receptor were performed as described (Radesca et al., 1991) with some modifications. In brief, brains from sigma receptor type I (σ1) knockout mice were homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates were then centrifuged at 1000 g for 10 mM at 4° C., and the supernatants were saved. The pellets were resuspended by vortexing in 2 mL/g ice-cold Tris-sucrose buffer and centrifuged again at 1000 g for 10 min. The combined 1000 g supernatants were centrifuged at 31000 g for 15 min at 4° C. The pellets were resuspended by vortexing in 3 mL/g 10 mM Tris-HCl, pH 7.4, and the suspension was kept at 25° C. for 15 min. Following centrifugation at 31000 g for 15 min, the pellets were resuspended by gentle Potter Elvehjem homogenization to a volume of 1.53 mL/g in 10 mM Tris-HCl pH 7.4.

The assay tubes contained 10 μL of [$^3$H]-DTG (final concentration of 3 nM), 400 μL of the tissue suspension (5.3 mL/g in 50 mM Tris-HCl, pH 8.0) to a final assay volume of 0.5 mL. Non-specific binding was defined by addition of a final concentration of 1 μM haloperidol. All tubes were incubated at 25° C. for 120 mM before termination of the reaction by rapid filtration over Schleicher & Schuell GF 3362 glass fibre filters [previously soaked in a solution of 0.5% polyethylenimine for at least 1 h]. Filters were washed with three times with 5 mL volumes of cold Tris-HCl buffer (10 mM, pH 8.0). Following addition of scintillation cocktail samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity c Receptor Ligands, *J. Med. Chem.* 34, 3065-3074.

Langa, F., Codony X., Tovar V., Lavado A., Giménez E., Cozar P., Cantero M., Dordal A., Hernández E., Pérez R., Monroy X., Zamanillo D., Guitart X., Montoliu Ll., 2003, Generation and phenotypic analysis of sigma receptor type I (Sigma1) knockout mice, *European Journal of Neuroscience*, Vol. 18, 2188-2196.

Lowry, O. H., N. J. Rosebrough, A. L. Farr, and R. J. Randall, 1951, Protein measurement with the Folin phenol reagent, *J. Biol. Chem*, 193, 265.

Some of the results obtained are shown in table (I).

TABLE (I)

| Example | % Binding σ1 $10^{-7}$ M | $K_i$ σ1 nM | % Binding σ2 $10^{-6}$ nM | $K_i$ σ2 nM |
|---|---|---|---|---|
| 1 | 102.1 | 1.54 | 3.7 | >10000 |
| 2 | 95.1 | | | |
| 3 | 102.3 | | | |
| 4 | 98.0 | | | |
| 5 | 107.5 | | | |
| 7 | 94.4 | | | |
| 8 | 94.5 | | | |
| 9 | 99.5 | | | |
| 13 | 50.9 | | | |
| 14 | 48.9 | | | |
| 16 | 46.5 | | | |
| 17 | 47.3 | | | |
| 18 | 58.6 | | | |
| 19 | 80.1 | | | |
| 21 | 45.5 | | | |
| 22 | 97.0 | 2.5 | | |
| 23 | 96.4 | 4.4 | | |
| 24 | 110 | 0.5 | | |
| 25 | 94.2 | 3.9 | | |
| 27 | 99.2 | 4.1 | | |
| 28 | 95.1 | | | |
| 30 | 83.0 | | | |
| 31 | 68.6 | | | |
| 32 | 72.7 | | | |
| 33 | 87.1 | | | |
| 34 | 103.8 | 12.4 | | |
| 35 | 101.7 | 8.6 | | |
| 36 | 52.7 | | | |
| 37 | 108.5 | | | |
| 38 | 108.1 | | | |
| 39 | 109.6 | | | |

TABLE (I)-continued

| Example | % Binding σ1 $10^{-7}$ M | $K_i$ σ1 nM | % Binding σ2 $10^{-6}$ nM | $K_i$ σ2 nM |
|---|---|---|---|---|
| 40 | 110.5 | | | |
| 61 | 93.6 | | | |
| 62 | 69.2 | | | |
| 63 | 105.2 | | | |
| 64 | 104.8 | | | |

Effect on Capsaicin in Development of Mechanical Allodynia

This model uses the von-Frey Filaments and is a model to test the effects or symptoms of neuropathic pain, allodynia etc.

Interest of the model:
The injection of 1 μg of capsaicin to experimental animals produces acute pain followed by hyperalgesia/allodynia The mechanisms involved in capsaicin-induced acute pain and hyperalgesia are relatively well known (mainly activation of peripheral nociceptors and sensitization of spinal cord neurons, respectively)

FIG. 1 shows the test protocol for all tests with von Frey filaments. After habituation mice were according to FIG. 1 first treated with the test-compound (or solvent in controls). Then 1 μg capsaicin (1% DMSO) is injected into their paw resulting in developing pain in the effected paw. The effected paw is then treated with a mechanical stimulus and the latency time before the paw is withdrawn is measured.

This pharmacological test showed the effect of the compound of example 1 (VII) in the model described.

Figure 2:
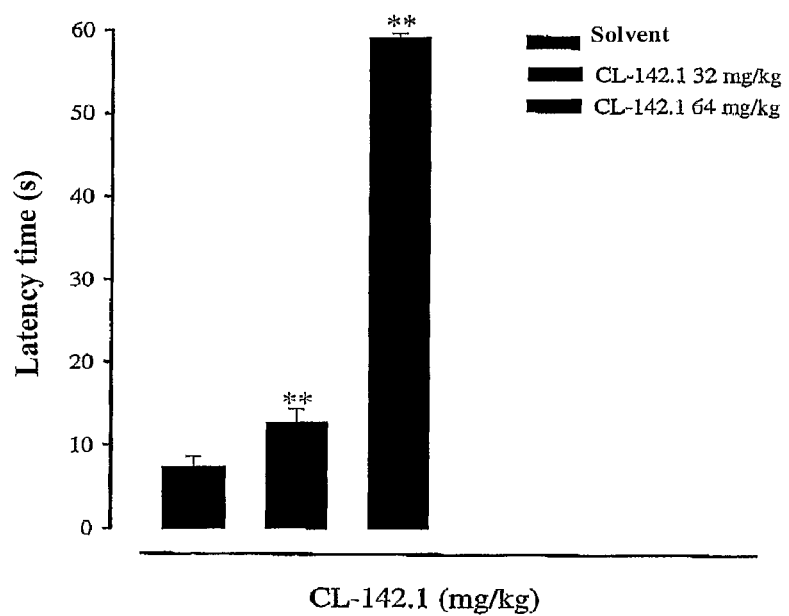
FIGS. 2 and 3 show the effect of the compound of example 1 (VII) in a model of neuropathic pain, especially mechanical allodynia.

As shown in FIG. 2 there is a dose dependency of the treatment with the compound of example 1 (VII) showing analgesia in capsaicin-induced neuropathic pain.

Figure 3:
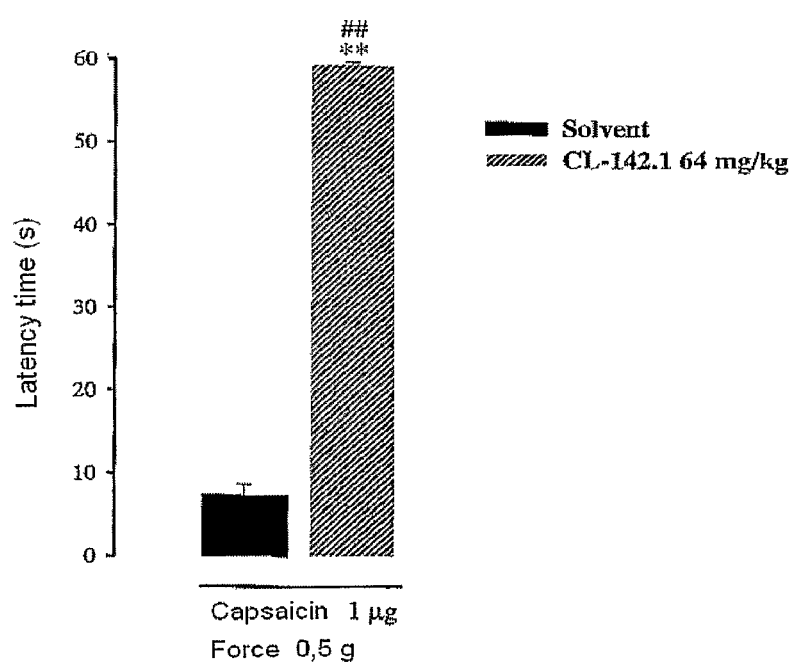

As demonstrated in FIG. 3 the treatment with the compound of example 1 (VII) is effective specifically in neuropathic pain or mechanical allodynia shown by the force of the von-Frey filaments with 0.5 g being typically in the range of neuropathic pain/allodynia.

The invention claimed is:

1. A compound of the formula I:

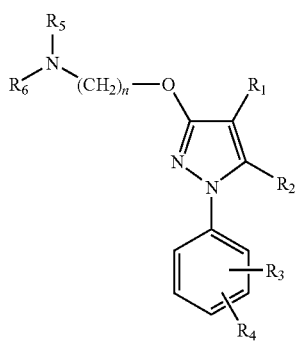

(I)

wherein
$R_1$ is selected from the group consisting of hydrogen, substituted or unsubstituted alkyl, substituted or unsubstituted cycloalkyl, substituted or unsubstituted alkenyl, substituted or unsubstituted arylalkyl, substituted or unsubstituted non-aromatic heterocyclyl, substituted or unsubstituted heterocyclylalkyl, —$COR_8$, —C(O)$OR_8$, —C(O)$NR_8R_9$, —CH=$NR_8$, —CN, —$OR_8$, —OC(O)$R_8$, —$NR_8R_9$, —$NR_8C(O)R_9$, —$NO_2$, —N=$CR_8R_9$, and halogen;

$R_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —C(O)$OR_8$, —CH=$NR_8$, —CN, —$OR_8$, —OC(O)$R_8$, —S(O)$_t$—$R_8$, —$NR_8R_9$, —$NR_8C(O)R_9$, —$NO_2$, —N=$CR_8R_9$, and halogen;

$R_3$ and $R_4$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —C(O)$OR_8$, —C(O)$NR_8R_9$, —CH=$NR_8$, —CN, —$OR_8$, —OC(O)$R_8$, —S(O)$_t$—$R_8$, —$NR_8R_9$, —$NR_8C(O)R_9$, —$NO_2$, —N=$CR_8R_9$, and halogen, or together they form a fused ring system, $R_5$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —C(O)$OR_8$, —C(O)$NR_8R_9$, —CH=$NR_8$, —CN, —$OR_8$, —OC(O)$R_8$, —S(O)$_t$—$R_8$, —$NR_8R_9$, —$NR_8C(O)R_9$, —$NO_2$, —N=$CR_8R_9$, and halogen;

$R_6$ is selected from the group consisting of hydrogen, substituted or unsubstituted ethyl, n-propyl, i-propyl, n-butyl, t-butyl or n-pentyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —C(O)$OR_8$, —C(O)$NR_8R_9$, —CH=$NR_8$, —CN, —$OR_8$, —OC(O)$R_8$, —S(O)$_t$—$R_8$, —$NR_8R_9$, —$NR_8C(O)R_9$, —$NO_2$, —N=$CR_8R_9$, and halogen;

n is 1 or 2;
t is 1 or 2;

$R_8$ and $R_9$ are each independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, and halogen;

or a pharmaceutically acceptable salt thereof.

2. The compound according to claim 1 wherein $R_1$ is H, —$COR_8$, or substituted or unsubstituted alkyl.

3. The compound according to claim 1 wherein $R_1$ is H, methyl or acetyl.

4. The compound according to claim 1 wherein $R_1$ is hydrogen.

5. The compound according to claim 1 wherein $R_2$ is H or alkyl.

6. The compound according to claim 1 wherein $R_2$ is methyl or H.

7. The compound according to claim 1 wherein $R_3$ and $R_4$ are situated in the meta and para positions of the phenyl group.

8. The compound according to claim 1 wherein $R_3$ and $R_4$ are independently selected from the group consisting of halogen, and substituted or unsubstituted alkyl.

9. The compound according to claim 1 wherein $R_3$ and $R_4$ are independently selected from the group consisting of halogen and haloalkyl.

10. The compound according to claim 1 wherein n is 2.

11. A compound according to claim 1 which is selected from the group consisting of:
- 2-[1-(3,4-Dichlorophenyl)-5-methyl-1H-pyrazol-3-yloxy]-N,N-diethylethanamine;
- 2-[1-(3,4-Dichlorophenyl)-5-isopropyl-1H-pyrazol-3-yloxy]-N,N-diethylethanamine;
- 2-[1-(3,4-dichlorophenyl)-1H-pyrazol-3-yloxy]-N,N-diethylethanamine;
- 2-[1-(3,4-Dichlorophenyl)-4,5-dimethyl-1H-pyrazol-3-yloxy]-N,N-diethylethanamine;
- 1-{1-(3,4-dichlorophenyl)-3-[2-(diethylamino)ethoxy]-5-methyl-1H-pyrazol-4-yl}ethanone; and
- N,N-Diethyl-2-[5-methyl-1-(naphthalen-2-yl)-1H-pyrazol-3-yloxy]ethanamine or a pharmaceutically acceptable salt thereof.

12. A pharmaceutical composition comprising the compound as defined in claim 1 and a pharmaceutically acceptable carrier, adjuvant or vehicle.

13. The compound according to claim 1 wherein $R_5$ and $R_6$ are both ethyl.

14. The compound according to claim 1 wherein $R_5$ is methyl and $R_6$ is benzyl.

* * * * *

UNITED STATES PATENT AND TRADEMARK OFFICE
CERTIFICATE OF CORRECTION

PATENT NO.        : 8,470,867 B2
APPLICATION NO.   : 12/703112
DATED             : June 25, 2013
INVENTOR(S)       : Christian Laggner et al.

Page 1 of 1

It is certified that error appears in the above-identified patent and that said Letters Patent is hereby corrected as shown below:

In the Specification

Column 1, lines 3 to 13, delete the paragraph beginning with "This application" and ending "in their entireties.", and insert the following paragraph:

--This application is a continuation of U.S. application Ser. No. 11/574,361, filed Aug. 9, 2007 now U.S. Patent No. 7,696,199. U.S. application Ser. No. 11/574,361 (now U.S. Patent No. 7,696,199) is a national stage entry under 35 U.S.C. §371 of International Application No. PCT/EP2005/009375 filed on Aug. 29, 2005, and is a continuation-in-part of U.S. application Ser. No. 10/978,250, filed on Oct. 29, 2004 (now abandoned). International Application No. PCT/EP2005/009375 claims benefit of Spanish Patent Application No. P200402441, filed on Oct. 14, 2004, European Patent Application No. 04077421.8, filed on Aug. 27, 2004, and U.S. application Ser. No. 10/978,250. U.S. application Ser. No. 10/978,250 claims benefit of European Patent Application No. 04077421.8. All of the foregoing patent documents are incorporated by reference in their entireties.--

Signed and Sealed this
Twenty-seventh Day of May, 2014

Michelle K. Lee
*Deputy Director of the United States Patent and Trademark Office*